(12) United States Patent
Kokuryo et al.

(10) Patent No.: US 7,772,794 B2
(45) Date of Patent: Aug. 10, 2010

(54) APPARATUS AND METHOD FOR CONTROLLING VEHICULAR WIPER

(75) Inventors: Kazuto Kokuryo, Shiga (JP); Yoshiteru Makino, Shiga (JP); Tetsuya Nakashima, Shiga (JP)

(73) Assignee: Niles Co., Ltd., Tokyo (JP)

( * ) Notice: Subject to any disclaimer, the term of this patent is extended or adjusted under 35 U.S.C. 154(b) by 281 days.

(21) Appl. No.: 12/084,540

(22) PCT Filed: Nov. 8, 2005

(86) PCT No.: PCT/JP2005/020477

§ 371 (c)(1),
(2), (4) Date: May 5, 2008

(87) PCT Pub. No.: WO2007/055001

PCT Pub. Date: May 18, 2007

(65) Prior Publication Data

US 2009/0134830 A1    May 28, 2009

(51) Int. Cl.
*B60S 1/08*    (2006.01)
(52) U.S. Cl. ............... 318/483; 318/444; 318/480; 250/208.1; 250/574
(58) Field of Classification Search .......... 318/444, 318/480, 483; 250/574, 208.1
See application file for complete search history.

(56) References Cited

U.S. PATENT DOCUMENTS

| | | | |
|---|---|---|---|
| 4,916,374 A | | 4/1990 | Schierbeek et al. |
| 5,059,877 A | * | 10/1991 | Teder .......... 318/444 |
| 5,276,389 A | | 1/1994 | Levers |
| 6,175,205 B1 | | 1/2001 | Michenfelder et al. |
| 6,331,819 B1 | | 12/2001 | Hog |
| 6,590,662 B2 | * | 7/2003 | Kokuryo et al. .......... 356/445 |
| 7,098,618 B2 | * | 8/2006 | Morishita ............ 318/444 |

(Continued)

FOREIGN PATENT DOCUMENTS

JP    3073632    6/2000

(Continued)

*Primary Examiner*—Paul Ip
(74) *Attorney, Agent, or Firm*—Hamre, Schumann, Mueller & Larson, P.C.

(57) ABSTRACT

A wiper controlling apparatus capable of discriminating between a signal change at the time of a wiper blade passage and that at the time of a raindrop impact so as to allow a wiper control promptly responding to the change in the condition of the sensing surface is provided. An estimating part (6) includes a displacement status data generating part (61) that calculates displacement status data representing a displacement status of the output signal of the photo-detector respectively based on a plurality of sampling data trains obtained at plural kinds of sampling periods in both of a period in which the wiper is in operation and a period in which the wiper is not in operation, a pattern data storing part (64) that stores in advance respective displacement status pattern data representing a displacement status of the output signal of the photo-detector when a lying object or a contact object is present on the sensing surface and when a wiper blade passes over the sensing surface, and a matching part (62) that compares the displacement status data calculated by the displacement status data generating part (61) with the displacement status pattern data in the pattern data storing part (64) and outputs the estimation result signal representing the condition of the sensing surface.

11 Claims, 21 Drawing Sheets

U.S. PATENT DOCUMENTS

| | | | |
|---|---|---|---|
| 7,154,241 B2 * | 12/2006 | Kokuryo et al. | 318/483 |
| 2001/0012106 A1 | 8/2001 | Kokuryo et al. | |
| 2004/0113578 A1 | 6/2004 | Kokuryo et al. | |
| 2005/0162116 A1 * | 7/2005 | Kokuryo et al. | 318/483 |
| 2005/0285557 A1 * | 12/2005 | Morishita | 318/444 |

FOREIGN PATENT DOCUMENTS

| | | |
|---|---|---|
| JP | 2001-180447 | 7/2001 |
| JP | 2001-518857 | 10/2001 |
| JP | 2002-277386 | 9/2002 |
| JP | 2003-306127 | 10/2003 |

* cited by examiner

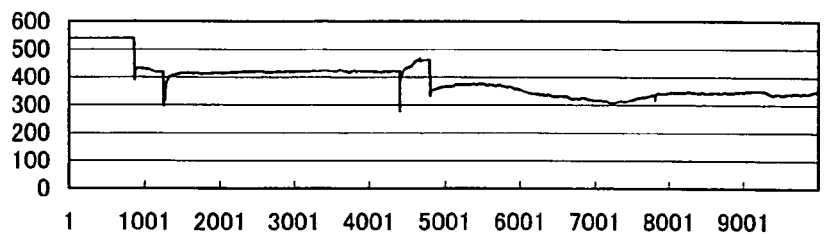
(a) PD output waveform (500 μs sampling)
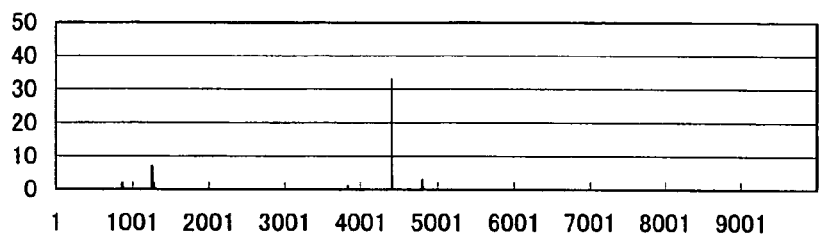
(b) Upward displacement amount (500 μs sampling)
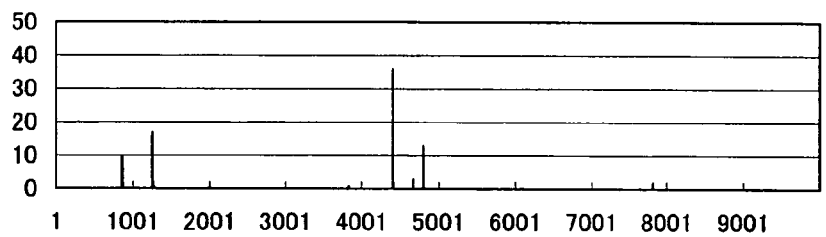
(c) Downward displacement amount (500 μs sampling)
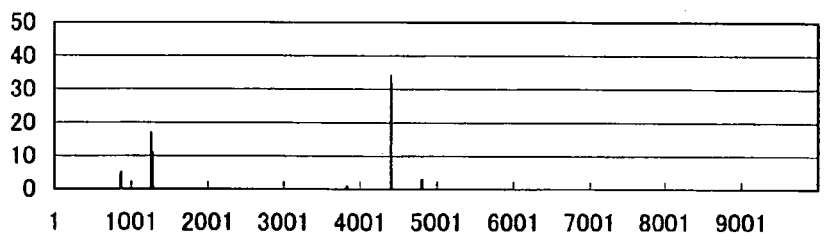
(d) Successive upward displacement amounts (500 μs sampling)
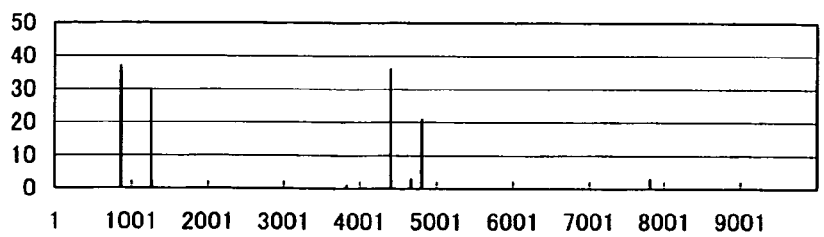
(e) Successive downward displacement amounts (500 μs sampling)
FIG. 9

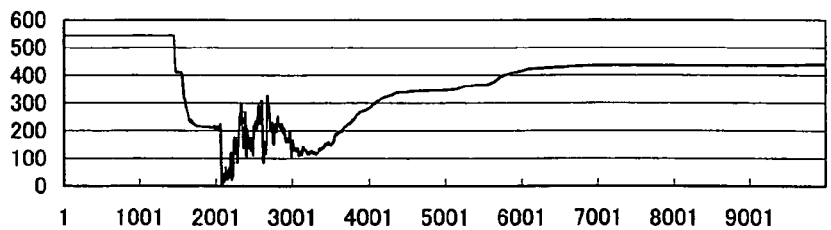
(a) PD output waveform (500 μs sampling)
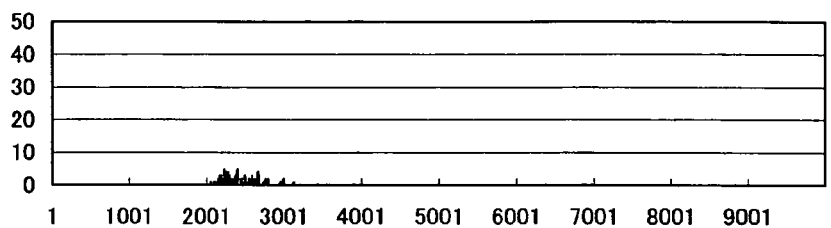
(b) Upward displacement amount (500 μs sampling)
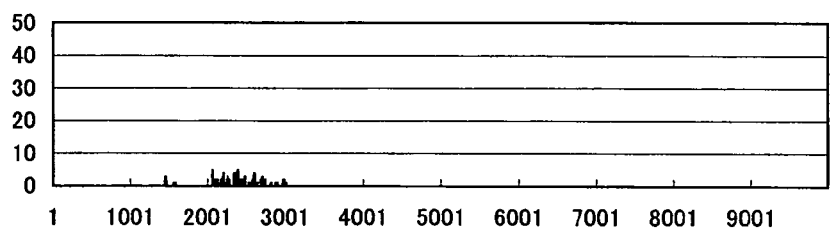
(c) Downward displacement amount (500 μs sampling)
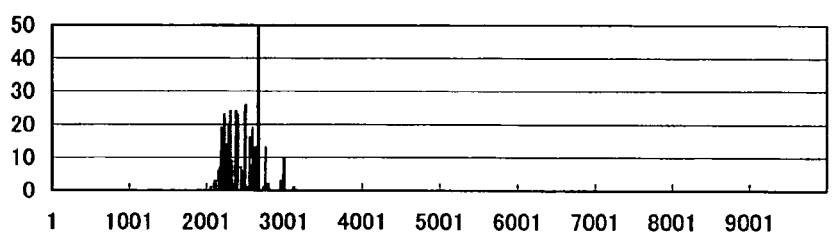
(d) Successive upward displacement amounts (500 μs sampling)
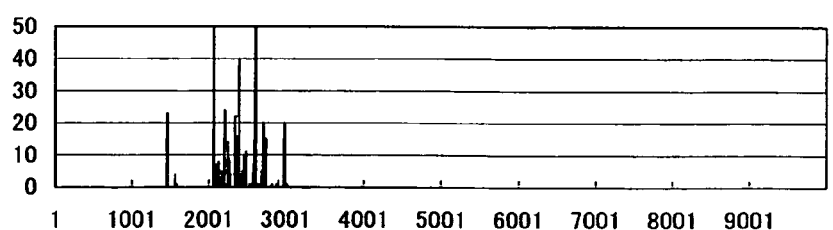
(e) Successive downward displacement amounts (500 μs sampling)
FIG. 10

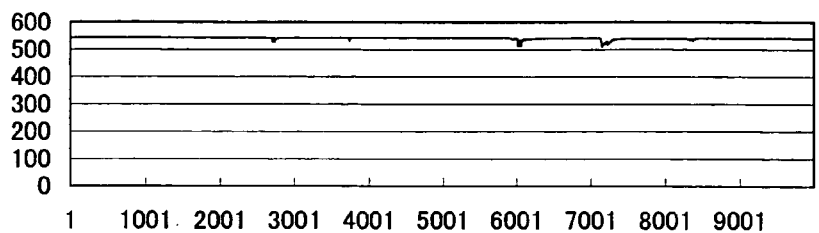
(a) PD output waveform (500 μs sampling)
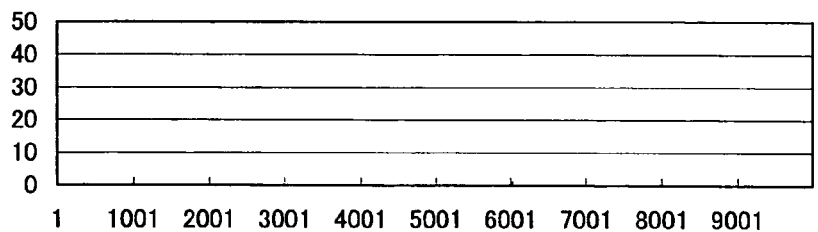
(b) Upward displacement amount (500 μs sampling)
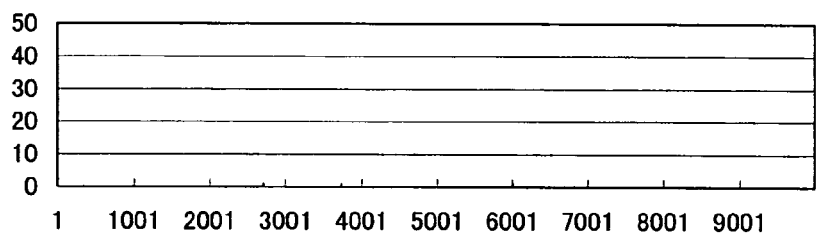
(c) Downward displacement amount (500 μs sampling)
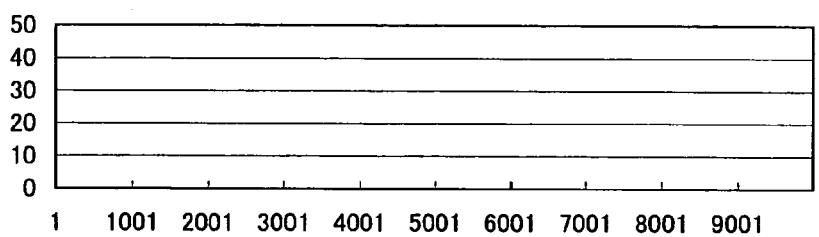
(d) Successive upward displacement amounts (500 μs sampling)
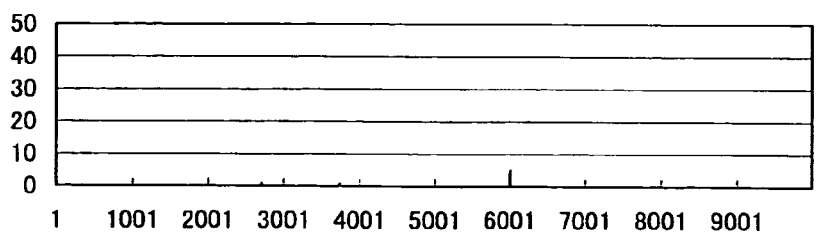
(e) Successive downward displacement amounts (500 μs sampling)
FIG. 11

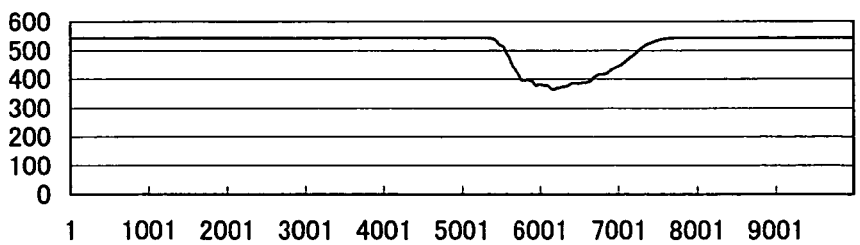
(a) PD output waveform (500 μs sampling)
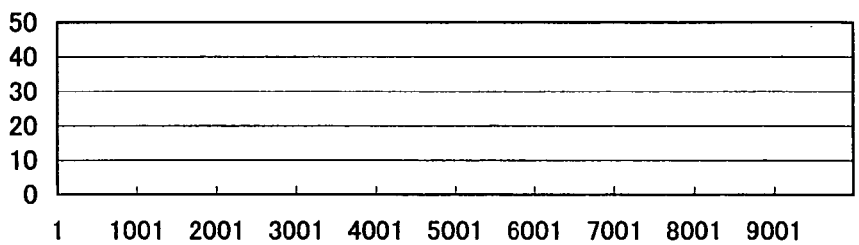
(b) Upward displacement amount (500 μs sampling)
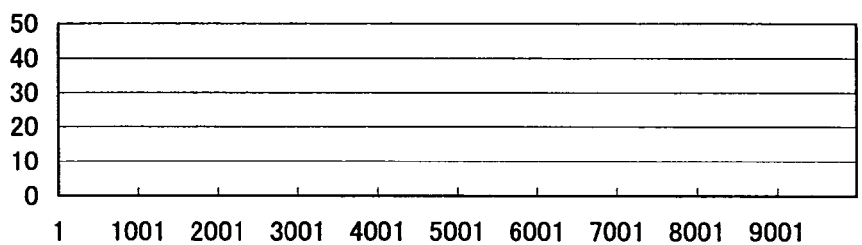
(c) Downward displacement amount (500 μs sampling)
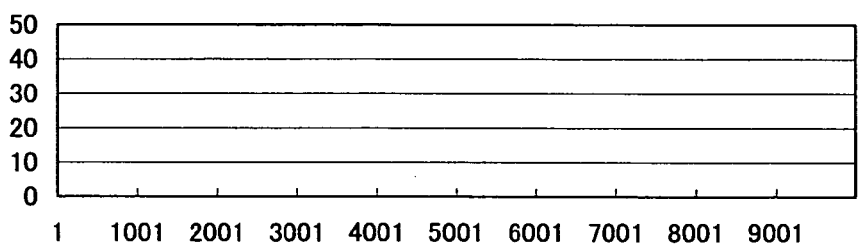
(d) Successive upward displacement amounts (500 μs sampling)
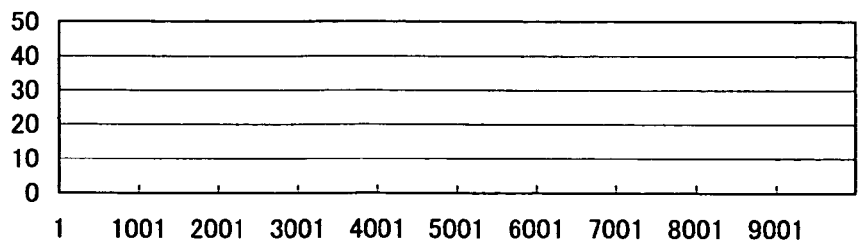
(e) Successive downward displacement amounts (500 μs sampling)
FIG. 12

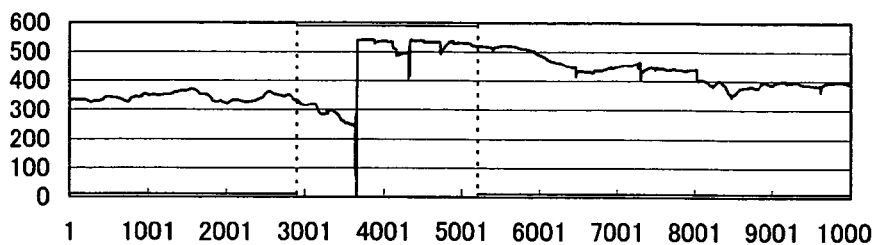
(a) PD output waveform (500 μs sampling)
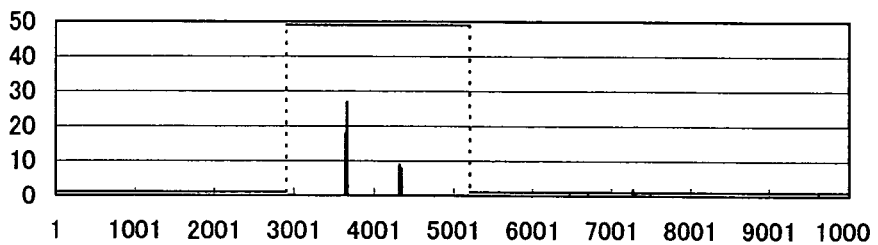
(b) Upward displacement amount (500 μs sampling)
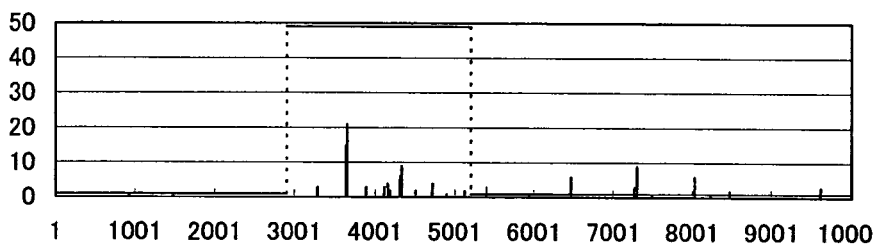
(c) Downward displacement amount (500 μs sampling)
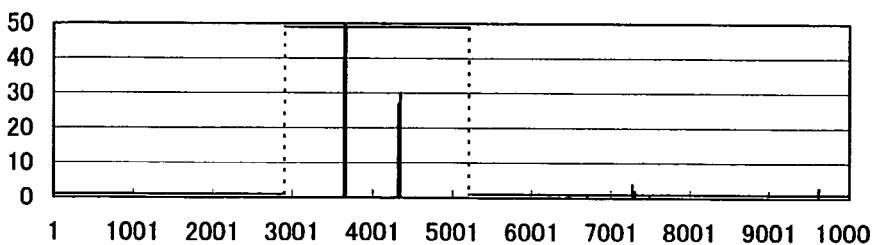
(d) Successive upward displacement amounts (500 μs sampling)
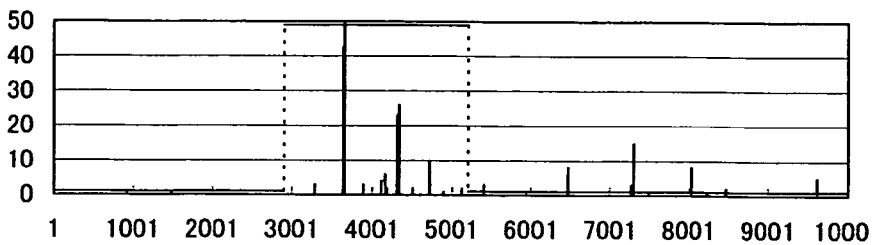
(e) Successive downward displacement amounts (500 μs sampling)
FIG. 13

| Sampling period | Displacement amount | Condition of sensing surface | | | | | |
|---|---|---|---|---|---|---|---|
| | | Raindrop impact | Running water passage | Finger contact | Condensation formation | Wiper passage | |
| 500 μs | Upward displacement amount (max.) | 33 | 5 | 0 | 0 | 27 | ⎫ |
| | Downward displacement amount (max.) | 36 | 5 | 0 | 0 | 21 | ⎬ d(N) |
| | Successive upward displacement amount (max.) | 34 | 48 | 2 | 0 | 134 | |
| | Successive downward displacement amount (max.) | 36 | 48 | 5 | 0 | 70 | ⎭ |
| 4ms | Upward displacement amount (max.) | 10 | 27 | 4 | 0 | 95 | ⎫ |
| | Downward displacement amount (max.) | 34 | 28 | 6 | 2 | 49 | ⎬ d(8N) |
| | Successive upward displacement amount (max.) | 20 | 53 | 4 | 0 | 114 | |
| | Successive downward displacement amount (max.) | 34 | 50 | 8 | 10 | 49 | ⎭ |
| 32ms | Upward displacement amount (max.) | 6 | 26 | 5 | 4 | 74 | ⎫ |
| | Downward displacement amount (max.) | 27 | 41 | 6 | 8 | 74 | ⎬ d(64N) |
| | Successive upward displacement amount (max.) | 13 | 47 | 6 | 30 | 30 | |
| | Successive downward displacement amount (max.) | 27 | 82 | 7 | 36 | 19 | ⎭ |
| 256ms | Upward displacement amount (max.) | 5 | 33 | 5 | 24 | 70 | ⎫ |
| | Downward displacement amount (max.) | 27 | 82 | 6 | 37 | 16 | ⎬ d(512N) |
| | Successive upward displacement amount (max.) | 7 | 80 | 5 | 40 | 70 | |
| | Successive downward displacement amount (max.) | 33 | 97 | 6 | 40 | 26 | ⎭ |

FIG. 14

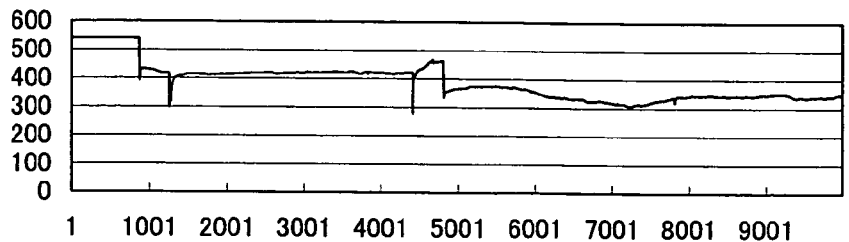
(a) PD value graph (4ms sampling)
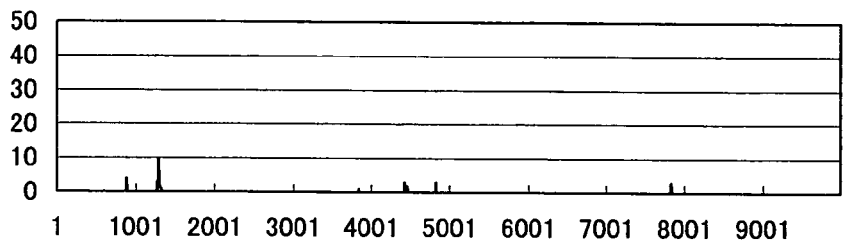
(b) Upward displacement amount (4ms sampling)
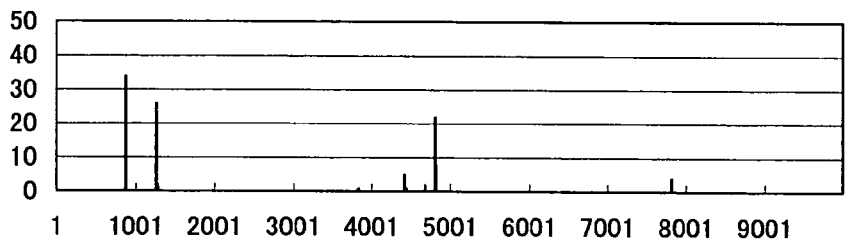
(c) Downward displacement amount (4ms sampling)
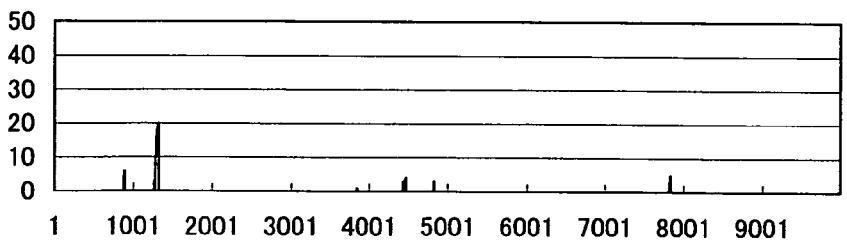
(d) Successive upward displacement amounts (4ms sampling)
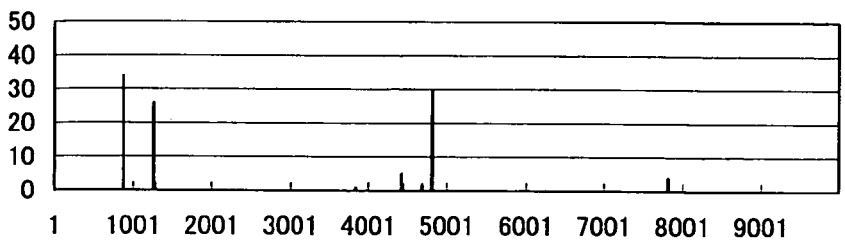
(e) Successive downward displacement amounts (4ms sampling)
FIG. 15

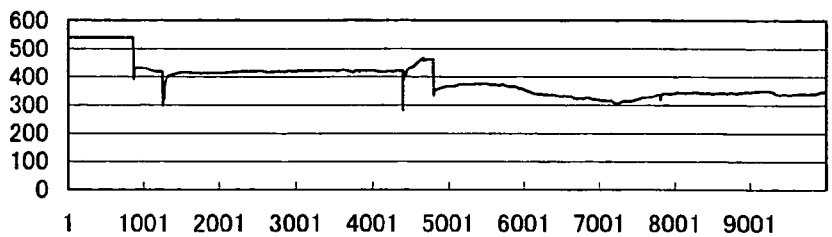
(a)  PD output waveform (32ms sampling)
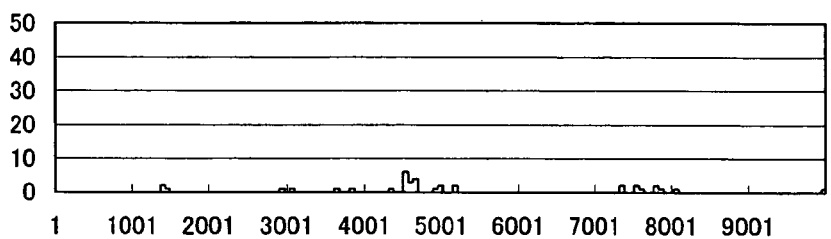
(b)  Upward displacement amount (32ms sampling)
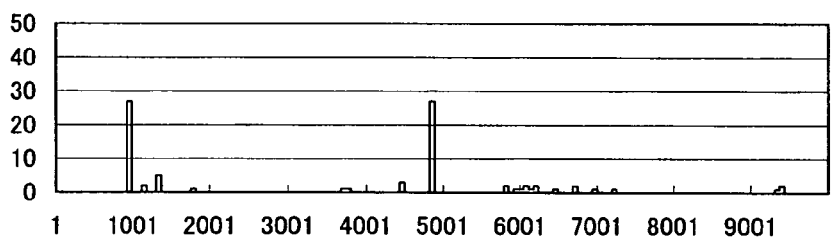
(c)  Downward displacement amount (32ms sampling)
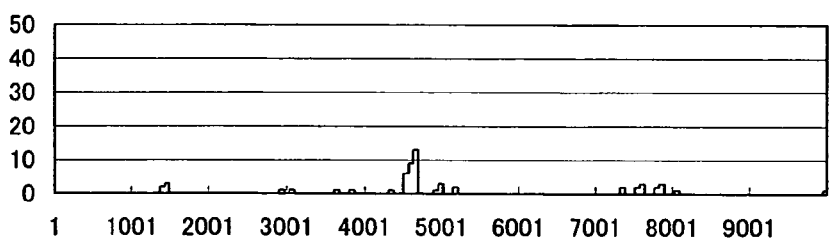
(d)  Successive upward displacement amounts (32ms sampling)
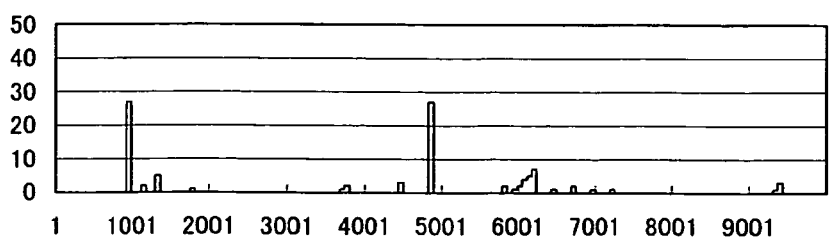
(e)  Successive downward displacement amounts (32ms sampling)
FIG. 16

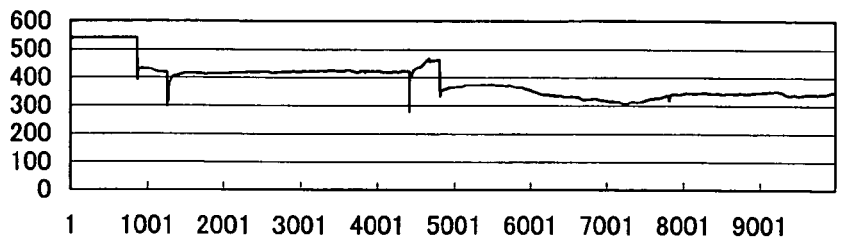
(a) PD value graph (256ms sampling)
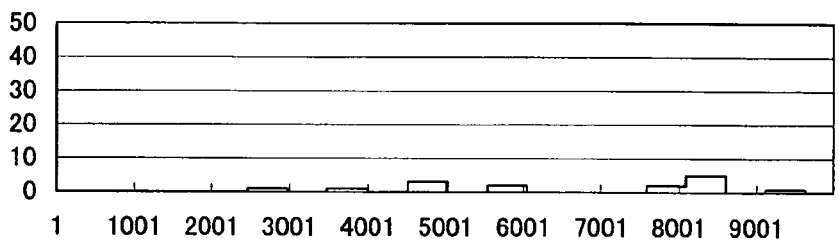
(b) Upward displacement amount (256ms sampling)
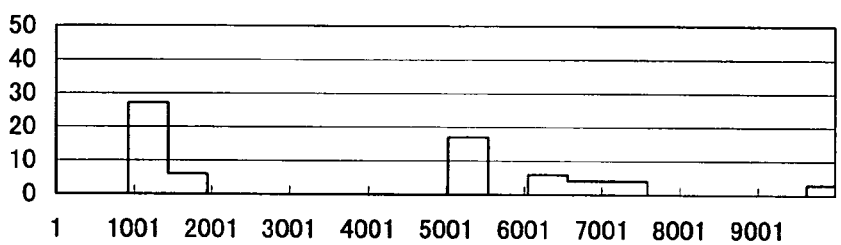
(c) Downward displacement amount (256ms sampling)
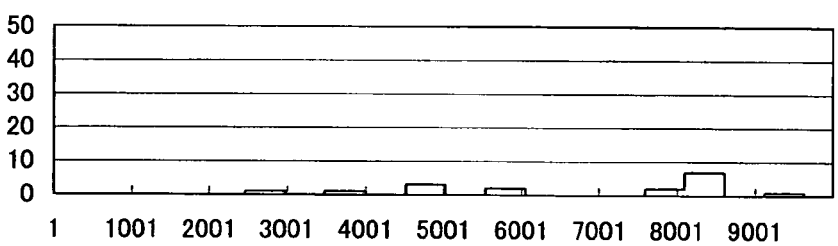
(d) Successive upward displacement amounts (256ms sampling)
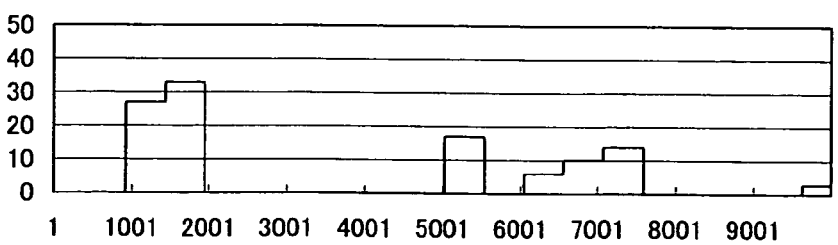
(e) Successive downward displacement amounts (256ms sampling)
FIG. 17

|  | | Condition of sensing surface | | | | | |
|---|---|---|---|---|---|---|---|
| Sampling period | Displacement amount | Raindrop impact | Running water passage | Finger contact | Condensation formation | Wiper passage | |
| 500 μs | Upward displacement amount (max.) | ☐ | ▲ | × | × | ■ | ⎫<br>⎬ d(N)<br>⎭ |
| | Downward displacement amount (max.) | ☐ | ▲ | × | × | ■ | |
| | Successive upward displacement amount (max.) | ☐ | ● | ▲ | × | ○ | |
| | Successive downward displacement amount (max.) | ☐ | ● | ▲ | × | ○ | |
| 4ms | Upward displacement amount (max.) | ▲ | ■ | ▲ | × | ○ | ⎫<br>⎬ d(8N)<br>⎭ |
| | Downward displacement amount (max.) | ☐ | ■ | ▲ | ▲ | ● | |
| | Successive upward displacement amount (max.) | △ | ○ | ▲ | × | ○ | |
| | Successive downward displacement amount (max.) | ☐ | ● | ▲ | ▲ | ● | |
| 32ms | Upward displacement amount (max.) | ▲ | ■ | ▲ | ▲ | ○ | ⎫<br>⎬ d(64N)<br>⎭ |
| | Downward displacement amount (max.) | ■ | ● | ▲ | ▲ | ○ | |
| | Successive upward displacement amount (max.) | △ | ● | ▲ | ☐ | ■ | |
| | Successive downward displacement amount (max.) | ■ | ○ | ▲ | ☐ | △ | |
| 256ms | Upward displacement amount (max.) | ▲ | ☐ | ▲ | ■ | ○ | ⎫<br>⎬ d(512N)<br>⎭ |
| | Downward displacement amount (max.) | ■ | ○ | ▲ | ☐ | △ | |
| | Successive upward displacement amount (max.) | ▲ | ○ | ▲ | ☐ | ○ | |
| | Successive downward displacement amount (max.) | ☐ | ○ | ▲ | ☐ | ■ | |

| Sign | Range of maximum value |
|---|---|
| × | 0 |
| ▲ | 1-10 |
| △ | 11-20 |
| ■ | 21-30 |
| ☐ | 31-40 |
| ● | 41-50 |
| ○ | 51 or more |

FIG. 18

| Sampling period | Displacement amount | Condition of sensing surface | | | | | |
|---|---|---|---|---|---|---|---|
| | | Raindrop impact | Running water passage | Finger contact | Condensation formation | Wiper passage | |
| 500 μs | Upward displacement amount (max.) | ○ | △ | × | × | △ | ⎫ |
| | Downward displacement amount (max.) | ○ | △ | × | × | △ | ⎬ d(N) |
| | Successive upward displacement amount (max.) | ○ | ○ | △ | × | ○ | |
| | Successive downward displacement amount (max.) | ○ | ○ | △ | × | ○ | ⎭ |
| 4ms | Upward displacement amount (max.) | △ | △ | △ | × | ○ | ⎫ |
| | Downward displacement amount (max.) | ○ | △ | △ | △ | ○ | ⎬ d(8N) |
| | Successive upward displacement amount (max.) | △ | ○ | △ | × | ○ | |
| | Successive downward displacement amount (max.) | ○ | ○ | △ | △ | ○ | ⎭ |
| 32ms | Upward displacement amount (max.) | △ | △ | △ | △ | ○ | ⎫ |
| | Downward displacement amount (max.) | △ | ○ | △ | △ | ○ | ⎬ d(64N) |
| | Successive upward displacement amount (max.) | △ | ○ | △ | △ | △ | |
| | Successive downward displacement amount (max.) | △ | ○ | △ | ○ | △ | ⎭ |
| 256ms | Upward displacement amount (max.) | △ | ○ | △ | △ | ○ | ⎫ |
| | Downward displacement amount (max.) | △ | ○ | △ | ○ | △ | ⎬ d(512N) |
| | Successive upward displacement amount (max.) | △ | ○ | △ | ○ | ○ | |
| | Successive downward displacement amount (max.) | ○ | ○ | △ | ○ | △ | ⎭ |

| Sign | Range of maximum value |
|---|---|
| × | 0 |
| △ | 1–30 |
| ○ | 31 or more |

FIG. 19

| Displacement amount component | Object / Sampling period | Raindrop | Wiper | Running water | Finger contact | Condensation formation | Status displacement data |
|---|---|---|---|---|---|---|---|
| Upward displacement amount | 500 μ sec | 2 | 3 | 1 | 1 | 0 | 3 |
| | 4msec | 3 | 5 | 1 | 1 | 0 | 1 |
| | 32msec | 3 | 5 | 2 | 1 | 1 | 1 |
| | 256msec | 1 | 5 | 5 | 1 | 3 | 1 |
| Downward displacement amount | 500 μ sec | 3 | 4 | 1 | 1 | 0 | 5 |
| | 4msec | 4 | 5 | 2 | 1 | 1 | 4 |
| | 32msec | 2 | 3 | 5 | 2 | 2 | 3 |
| | 256msec | 2 | 4 | 5 | 2 | 5 | 2 |
| Successive upward displacement amount | 500 μ sec | 3 | 5 | 1 | 1 | 0 | 3 |
| | 4msec | 5 | 5 | 5 | 1 | 0 | 2 |
| | 32msec | 5 | 5 | 5 | 2 | 5 | 2 |
| | 256msec | 5 | 5 | 5 | 1 | 5 | 2 |
| Successive downward displacement amount | 500 μ sec | 4 | 5 | 3 | 1 | 0 | 5 |
| | 4msec | 5 | 5 | 5 | 2 | 2 | 4 |
| | 32msec | 3 | 3 | 5 | 2 | 5 | 3 |
| | 256msec | 4 | 4 | 5 | 2 | 5 | 3 |
| Number of successive upward displacements | 500 μ sec | 1 | 2 | 2 | 1 | 0 | 1 |
| | 4msec | 1 | 1 | 5 | 1 | 0 | 2 |
| | 32msec | 1 | 1 | 4 | 1 | 5 | 1 |
| | 256msec | 1 | 1 | 1 | 1 | 1 | 2 |
| Number of successive downward displacements | 500 μ sec | 1 | 2 | 4 | 2 | 0 | 2 |
| | 4msec | 1 | 1 | 4 | 1 | 2 | 1 |
| | 32msec | 1 | 1 | 1 | 1 | 3 | 1 |
| | 256msec | 2 | 1 | 1 | 1 | 1 | 1 |
| Difference between upward displacement amounts (increase) | 500 μ sec | 2 | 2 | 1 | 1 | 0 | 3 |
| | 4msec | 3 | 5 | 1 | 1 | 0 | 1 |
| | 32msec | 3 | 5 | 2 | 1 | 1 | 1 |
| | 256msec | 1 | 5 | 4 | 1 | 2 | 1 |
| Difference between upward displacement amounts (decrease) | 500 μ sec | 2 | 2 | 1 | 1 | 0 | 3 |
| | 4msec | 3 | 5 | 1 | 1 | 0 | 1 |
| | 32msec | 3 | 5 | 2 | 1 | 1 | 1 |
| | 256msec | 1 | 5 | 5 | 1 | 3 | 1 |
| Difference between downward displacement amounts (increase) | 500 μ sec | 3 | 2 | 1 | 1 | 0 | 5 |
| | 4msec | 4 | 5 | 1 | 1 | 1 | 4 |
| | 32msec | 2 | 2 | 4 | 2 | 1 | 3 |
| | 256msec | 2 | 1 | 5 | 1 | 5 | 2 |
| Difference between downward displacement amounts (decrease) | 500 μ sec | 4 | 2 | 1 | 1 | 0 | 5 |
| | 4msec | 4 | 5 | 1 | 1 | 1 | 4 |
| | 32msec | 2 | 2 | 4 | 2 | 1 | 3 |
| | 256msec | 2 | 3 | 5 | 1 | 5 | 2 |

| Displacement amount component | Object / Sampling period | Raindrop | Wiper | Running water | Finger contact | Condensation formation |
|---|---|---|---|---|---|---|
| Upward displacement amount | 500 μ sec | 1 | 0 | 2 | 2 | 3 |
| | 4msec | 2 | 4 | 0 | 0 | 1 |
| | 32msec | 2 | 4 | 1 | 0 | 0 |
| | 256msec | 0 | 4 | 4 | 0 | 2 |
| Downward displacement amount | 500 μ sec | 2 | 1 | 4 | 4 | 5 |
| | 4msec | 0 | 1 | 2 | 3 | 3 |
| | 32msec | 1 | 0 | 2 | 1 | 1 |
| | 256msec | 0 | 2 | 3 | 0 | 3 |
| Successive upward displacement amount | 500 μ sec | 0 | 2 | 2 | 2 | 3 |
| | 4msec | 3 | 3 | 3 | 1 | 2 |
| | 32msec | 3 | 3 | 3 | 0 | 3 |
| | 256msec | 3 | 3 | 3 | 1 | 3 |
| Successive downward displacement amount | 500 μ sec | 1 | 0 | 2 | 4 | 5 |
| | 4msec | 1 | 1 | 1 | 2 | 2 |
| | 32msec | 0 | 0 | 2 | 1 | 2 |
| | 256msec | 1 | 1 | 2 | 1 | 2 |
| Number of successive upward displacements | 500 μ sec | 0 | 1 | 1 | 0 | 1 |
| | 4msec | 1 | 1 | 3 | 1 | 2 |
| | 32msec | 0 | 0 | 3 | 0 | 4 |
| | 256msec | 1 | 1 | 1 | 1 | 1 |
| Number of successive downward displacements | 500 μ sec | 1 | 0 | 2 | 0 | 2 |
| | 4msec | 0 | 0 | 3 | 0 | 1 |
| | 32msec | 0 | 0 | 0 | 0 | 2 |
| | 256msec | 1 | 0 | 0 | 0 | 0 |
| Difference between upward displacement amounts (increase) | 500 μ sec | 1 | 1 | 2 | 2 | 3 |
| | 4msec | 2 | 4 | 0 | 0 | 1 |
| | 32msec | 2 | 4 | 1 | 0 | 0 |
| | 256msec | 0 | 4 | 3 | 0 | 1 |
| Difference between upward displacement amounts (decrease) | 500 μ sec | 1 | 1 | 2 | 2 | 3 |
| | 4msec | 2 | 4 | 0 | 0 | 1 |
| | 32msec | 2 | 4 | 1 | 0 | 0 |
| | 256msec | 0 | 4 | 4 | 0 | 2 |
| Difference between downward displacement amounts (increase) | 500 μ sec | 2 | 3 | 4 | 4 | 5 |
| | 4msec | 0 | 1 | 3 | 3 | 3 |
| | 32msec | 1 | 1 | 1 | 1 | 2 |
| | 256msec | 0 | 1 | 3 | 1 | 3 |
| Difference between downward displacement amounts (decrease) | 500 μ sec | 1 | 3 | 4 | 4 | 5 |
| | 4msec | 0 | 1 | 3 | 3 | 3 |
| | 32msec | 1 | 1 | 1 | 1 | 2 |
| | 256msec | 0 | 1 | 3 | 1 | 3 |

FIG. 21

Results of displacement amount determining processing based on PD value for individual sampling periods

| | |
|---|---|
| 0 | : No change |
| 1 | : Change 1 |
| 2 | : Change 2 |
| 3 | : Change 3 |
| 4 | : Change 4 |
| 5 | : Change 5 or more |

| Displacement amount component | Kind of object / Sampling period | Raindrop (hydrophilic) | Raindrop (water repellent) | Wiper (hydrophilic) | Wiper (water repellent) | Running water | Finger contact | Condensation formation |
|---|---|---|---|---|---|---|---|---|
| Upward displacement amount | 500 μ sec | 2 | 1 | 3 | 1 | 1 | 1 | 0 |
| | 4msec | 3 | 2 | 5 | 3 | 1 | 1 | 0 |
| | 32msec | 3 | 1 | 5 | 2 | 2 | 1 | 1 |
| | 256msec | 1 | 1 | 5 | 1 | 5 | 1 | 3 |
| Downward displacement amount | 500 μ sec | 3 | 1 | 4 | 1 | 1 | 1 | 0 |
| | 4msec | 4 | 2 | 5 | 3 | 2 | 1 | 1 |
| | 32msec | 2 | 1 | 3 | 2 | 5 | 2 | 2 |
| | 256msec | 2 | 1 | 4 | 1 | 5 | 2 | 5 |
| Successive upward displacement amount | 500 μ sec | 3 | 3 | 5 | 3 | 1 | 1 | 0 |
| | 4msec | 5 | 3 | 5 | 3 | 5 | 1 | 0 |
| | 32msec | 5 | 1 | 5 | 2 | 5 | 2 | 5 |
| | 256msec | 5 | 2 | 5 | 1 | 5 | 1 | 5 |
| Successive downward displacement amount | 500 μ sec | 4 | 2 | 5 | 3 | 3 | 1 | 0 |
| | 4msec | 5 | 3 | 5 | 3 | 5 | 2 | 2 |
| | 32msec | 3 | 1 | 3 | 2 | 5 | 2 | 5 |
| | 256msec | 4 | 1 | 4 | 1 | 5 | 2 | 5 |
| Number of successive upward displacements | 500 μ sec | 1 | 4 | 2 | 2 | 2 | 1 | 0 |
| | 4msec | 1 | 1 | 1 | 1 | 5 | 1 | 0 |
| | 32msec | 1 | 1 | 1 | 1 | 4 | 1 | 5 |
| | 256msec | 1 | 1 | 1 | 1 | 1 | 1 | 1 |
| Number of successive downward displacements | 500 μ sec | 1 | 3 | 2 | 2 | 4 | 2 | 0 |
| | 4msec | 1 | 1 | 1 | 1 | 4 | 1 | 2 |
| | 32msec | 1 | 1 | 1 | 1 | 1 | 1 | 3 |
| | 256msec | 2 | 1 | 1 | 1 | 1 | 1 | 1 |
| Difference between upward displacement amounts (increase) | 500 μ sec | 2 | 1 | 2 | 1 | 1 | 1 | 0 |
| | 4msec | 3 | 1 | 5 | 3 | 1 | 1 | 0 |
| | 32msec | 3 | 1 | 5 | 2 | 2 | 1 | 1 |
| | 256msec | 1 | 1 | 5 | 1 | 4 | 1 | 2 |
| Difference between upward displacement amounts (decrease) | 500 μ sec | 2 | 1 | 2 | 1 | 1 | 1 | 0 |
| | 4msec | 3 | 1 | 5 | 3 | 1 | 1 | 0 |
| | 32msec | 3 | 1 | 5 | 2 | 2 | 1 | 1 |
| | 256msec | 1 | 1 | 5 | 1 | 5 | 1 | 3 |
| Difference between downward displacement amounts (increase) | 500 μ sec | 3 | 1 | 2 | 1 | 1 | 1 | 0 |
| | 4msec | 4 | 1 | 5 | 3 | 1 | 1 | 1 |
| | 32msec | 2 | 1 | 2 | 2 | 4 | 2 | 1 |
| | 256msec | 2 | 1 | 1 | 1 | 5 | 1 | 5 |
| Difference between downward displacement amounts (decrease) | 500 μ sec | 4 | 1 | 2 | 1 | 1 | 1 | 0 |
| | 4msec | 4 | 1 | 5 | 3 | 1 | 1 | 1 |
| | 32msec | 2 | 1 | 2 | 2 | 4 | 2 | 1 |
| | 256msec | 2 | 1 | 3 | 1 | 5 | 1 | 5 |

FIG. 22

APPARATUS AND METHOD FOR CONTROLLING VEHICULAR WIPER

TECHNICAL FIELD

The present invention relates to a vehicular wiper controlling apparatus, and in particular, a vehicular wiper controlling apparatus characterized by its raindrop sensing and control.

BACKGROUND ART

Conventionally, many wiper controlling apparatuses used in vehicles have been suggested. In such wiper controlling apparatuses, one of the important factors is a mechanism of sensing raindrops, which is called a rain sensor. As a structural example of a rain sensor using an optical system, there is a known configuration in which light emitted from a photo emission element is reflected by a sensing surface provided on a windshield, and then received by a photo-detector, thereby sensing raindrops. In other words, the photo emission element, the sensing surface and the photo-detector are arranged such that the light reflected by the sensing surface reaches the photo-detector in the state where no object is lying on the sensing surface. Then, when water or the like impacts on the sensing surface, the reflection condition on this surface changes, whereby the amount of light reaching the photo-detector decreases, resulting in a lowered output of the photo-detector. Raindrops have been sensed by recognizing this change.

In the conventional configuration described above, the changes in the light amount often have been identified by the photo-detector by a system of comparison with a predetermined reference value (a threshold method).

Now, these wiper controlling apparatuses are used under various conditions in practice. Therefore, measures have to be taken to prevent their malfunction. Thus, in the rain sensor, a plurality of reference values have been set according to various modes, or the reference value has been updated sequentially according to situations.

In the conventional rain sensor described above, the logic of sensing raindrops has become more complex, thus making it difficult to process the detection judgment at a high speed. Furthermore, all these methods basically judge the condition of the sensing surface and detect raindrops by comparison with the reference value. Therefore, owing to the influence of external light and conditions of the sensing surface such as dirt, it has been difficult to prevent the malfunction completely.

In order to solve such problems, the inventors of the present invention suggested a sensing device and a wiper controlling apparatus using the same, etc. in JP 2001-180447 A, JP 2002-277386 A and JP 2003-306127 A.

JP 2001-180447 A mentioned above disclosed "an object sensor sensing the status of a sensing surface by detecting a light with a photo detector, which light has been emitted by a photo emission element and reflected on the sensing surface, comprising: a means for generating a time lag signal from the output signal of the photo detector; a means for calculating a differential signal between the output signal of the photo detector and the time lag signal; and a means for judging the status of the sensing surface by detecting the generation of the differential signal."

This technology was characterized by the ability to detect instantly a dynamic process of an impacting raindrop, etc. itself, which was not possible by the conventional technology.

Also, JP 2002-277386 A disclosed "a sensing device in which a light emitted from a light-emitting member is introduced to a transparent plate, reflected by a sensing surface of the transparent plate and then received by a photo-detector, thereby detecting a condition of an object that has impacted on the sensing surface, the sensing device comprising: a sampling part for sampling signals from the photo-detector; a fluctuation sensing part for sensing a fluctuation of the signals from the photo-detector; and a judging part for judging the object based on a changing pattern of the signal fluctuation sensed by the fluctuation sensing part."

The characteristics of this technology follow. That is, with a dynamic fluctuation of the signal of the photo-detector obtained through the object that has impacted on the sensing surface, it is possible to sense a dynamic jiggling of the lying object indirectly. Furthermore, with the changing pattern of the signal fluctuation, the changing pattern of the lying object's jiggling determined by the lying object's physical properties can be sensed indirectly, thus making it possible to judge the kind and condition of the lying object.

Moreover, in the technology disclosed in JP 2003-306127 A, the two technologies described above are combined so as to control a wiper.

Other than the above, a wiper operating device disclosed in JP 2001-518857 A (WO 98/45148) can perform fog and drizzle identification in addition to rain identification and water droplet identification. In this device, the measurement values of a moisture sensor are associated with incremental values. Each difference value between two successive incremental values is added to the sum of difference values that are signed and previously formed in a similar manner in a memory, and used for controlling a wiping operation.

Additionally, JP 3073632 B discloses "a method comprising the steps of detecting the presence of a falling edge in the sensor signal, the falling edge indicating the presence of moisture on the monitored portion of the windshield; identifying the shape of the falling edge, the wiping system detecting a rain pattern based on the shape and number of falling edges in the sensor signal during a predetermined period of time; and controlling the windshield wiping system based on the identified rain pattern."

Patent document 1: JP 2001-180447 A

Patent document 2: JP 2002-277386 A

Patent document 3: JP 2003-306127 A

Patent document 4: JP 2001-518857 A

Patent document 5: JP 3073632 B

DISCLOSURE OF INVENTION

Problem to be Solved by the Invention

With each instance of the wiping operation by the wiper, a wiper blade passes over the sensing surface of the above-described rain sensor. The conventional rain sensor cannot discriminate between a signal change of the photo-detector caused by the passage of the wiper blade over the sensing surface and a signal change when a raindrop or the like impacts on the sensing surface, and thus ends up misjudging the wiper blade passage to be the raindrop impact. Accordingly, in the conventional wiper controlling apparatus, a signal from the photo-detector at the time of the wiper blade passage has not been processed. In other words, during a period in which the wiper is in operation, the signal from the photo-detector has been masked.

A wiper driving apparatus has a mechanism for maintaining the operation of a motor until the wiper blade returns to a resting position (received position) without stopping the wiping operation even when the switch is turned off during the wiper operation. In other words, the wiper driving apparatus outputs a signal indicating that the wiper is in operation (a wiper operation signal).

The conventional wiper controlling apparatus has utilized this wiper operation signal in order to mask the signal from the photo-detector easily. In other words, the conventional wiper controlling apparatus has utilized the wiper operation signal so as to recognize the start of driving of the wiper, thereby determining the period for masking the signal from the photo-detector.

Herein, the case in which a rainfall condition changes abruptly is assumed. For example, immediately after the wiping operation begins, it suddenly starts raining very hard. Such a situation often occurs when a vehicle comes out through a tunnel and arrives under a torrential rain, or the like. In such a case, even after the wiper carries out the wiping operation to wipe off raindrops on the sensing surface, thereby initializing the sensing surface, raindrops impact on the sensing surface again shortly. Consequently, by the time the wiper blade returns to the resting position, the sensing surface already is covered with raindrops. When the wiper blade returns to the resting position, the wiper operation signal is turned OFF. Then, with the condition of the sensing surface at that time serving as an initial condition, the operation of detecting a raindrop by the rain sensor is started. However, at this time, the sensing surface is already covered with the raindrops as described above. Therefore, the operation of detecting a raindrop is started with a lowered sensitivity of the rain sensor.

In this case, the rain sensor cannot fully grasp the lying condition of the raindrop. Thus, in many cases, the wiper is not operated at the timing desired by a driver in spite of the fact that, since a substantial amount of the raindrops lies on the windshield, the wiper has to be operated quickly to wipe off the raindrops.

Besides the heavy rain after passing through a tunnel, examples of the case in which it is preferable to operate the wiper promptly to respond to the abrupt change in the condition of the sensing surface include the case where the sensing surface is splashed by a truck or the like, the case where a large amount of raindrops that have accumulated on a vehicular roof runs onto the sensing surface and obstructs the view, the case where the windshield fogs instantly when the vehicle enters a tunnel with a high humidity, etc. Conventionally, it has been difficult to grasp such abrupt changes in the condition of the sensing surface because the output signal is masked during the wiper operation.

Of course, it is possible to shorten the masking period by, for example, providing a rotation shaft of the wiper with a position detection sensor so as to grasp minutely the period in which the wiper blade passes over the sensing surface. However, such a technique is not preferable due to its high cost, and the masking period still is provided. Incidentally, the masking period of course has been provided in the conventional threshold method and also necessary in the conventional technologies suggested by the inventors of the present invention.

As described above, the conventional wiper controlling apparatuses have had to mask the signal from the photo-detector during the period in which the wiper blade passes over the sensing surface. As a result, an inherent sensitivity of the rain sensor has been impaired, making it difficult to control the wiper promptly in response to the change in the condition of the sensing surface.

The present invention was made in view of the problems described above. It is an object of the present invention to provide a wiper controlling apparatus capable of discriminating between a signal change at the time of a wiper blade passage and a signal change at the time of a raindrop impact by contriving signal processing to estimate an object lying on a sensing surface, so as to allow a wiper control promptly responding to the change in the condition of the sensing surface.

Means for Solving Problem

In order to achieve the above-mentioned object, a vehicular wiper controlling apparatus according to the present invention includes an optical part including a photo emission element that irradiates light to a sensing surface, and a photo-detector that is arranged at a position receiving the light emitted from the photo emission element and reflected by the sensing surface, the sensing surface being part of a surface of a windshield glass of a vehicle; an estimating part that estimates a condition of the sensing surface by analyzing a change in an output signal of the photo-detector; and a wiper controlling part that controls an operation of a wiper installed in the vehicle according to an estimation result signal outputted from the estimating part. The estimating part includes a displacement status data generating part that calculates displacement status data representing a displacement status of the output signal of the photo-detector respectively based on a plurality of sampling data trains obtained from the output signal of the photo-detector at plural kinds of sampling periods in both of a period in which the wiper is in operation and a period in which the wiper is not in operation, a pattern data storing part that stores in advance displacement status pattern data representing a displacement status of the output signal of the photo-detector when a lying object or a contact object is present on the sensing surface and displacement status pattern data representing a displacement status of the output signal of the photo-detector when a wiper blade passes over the sensing surface, and a matching part that compares the displacement status data calculated by the displacement status data generating part with the displacement status pattern data stored in the pattern data storing part and outputs the estimation result signal representing the condition of the sensing surface.

Incidentally, the "lying object" mentioned above refers to an object or a material that stays on the sensing surface at least temporarily, and also includes the one that moves from its initial impact position. The "contact object" mentioned above includes the one that contacts the sensing surface at least temporarily and moves over the sensing surface, and also includes the one that passes over the sensing surface such as running water, a human finger or a wiper blade.

With the above configuration, it is possible to calculate the displacement status data representing the displacement status of the output signal of the photo-detector respectively based on a plurality of sampling data trains obtained at plural kinds of sampling periods and compare them with the displacement status pattern data stored in advance in the pattern data storing part, thereby estimating the condition of the sensing surface throughout the entire period of both the period in which the wiper is in operation and the period in which the wiper is not in operation. Consequently, a wiper controlling apparatus that achieves a wiper control promptly responding to the change in the condition of the sensing surface can be provided.

In the vehicular wiper controlling apparatus according to the present invention, it is preferable that the pattern data storing part stores in advance plural kinds of displacement status pattern data regarding a form of water lying on or contacting the sensing surface as the displacement status pattern data representing the displacement status of the output signal of the photo-detector when the lying object or the contact object is present on the sensing surface.

In the vehicular wiper controlling apparatus according to the present invention, it is preferable that the displacement status data generating part generates a sampling data train consisting of m sampling data (where $m=2^{a \times b}$, with a and b being an integer) obtained at a predetermined clock period N and a sampling data train consisting of $2^b$, $2^{b-1}$, ..., $(m/2^{a \times c})$ sampling data obtained at clock periods obtained by multiplying the clock period N respectively by $2^a$, $2^{a \times 2}$, ..., $2^{a \times c}$ (where c is an integer not greater than b) as the plurality of sampling data trains.

In the vehicular wiper controlling apparatus according to the present invention, it is preferable that the displacement status data generating part calculates displacement amounts of sampling data respectively in the plurality of sampling data trains as the displacement status data.

In the vehicular wiper controlling apparatus according to the present invention, it is preferable that the displacement status data generating part calculates a displacement amount difference representing a difference between displacement amounts of sampling data respectively in the plurality of sampling data trains as the displacement status data.

In the vehicular wiper controlling apparatus according to the present invention, it is preferable that the displacement status data generating part calculates successive displacement amounts representing an amount by which the sampling data are displaced successively in either a positive direction or a negative direction respectively in the plurality of sampling data trains as the displacement status data.

In the vehicular wiper controlling apparatus according to the present invention, it is preferable that the displacement status data generating part calculates the number of successive displacements representing the number of times by which the sampling data are displaced successively in either a positive direction or a negative direction respectively in the plurality of sampling data trains as the displacement status data.

In the vehicular wiper controlling apparatus according to the present invention, it is preferable that the pattern data storing part stores in advance displacement status pattern data representing a displacement status of the output signal of the photo-detector when a lying object or a contact object is present on a water-repellent sensing surface, displacement status pattern data representing a displacement status of the output signal of the photo-detector when the wiper blade passes over a water-repellent sensing surface, displacement status pattern data representing a displacement status of the output signal of the photo-detector when a lying object or a contact object is present on a hydrophilic sensing surface and displacement status pattern data representing a displacement status of the output signal of the photo-detector when the wiper blade passes over a hydrophilic sensing surface.

The "water-repellent (hydrophilic) sensing surface" mentioned above includes a sensing surface in both of the cases where a surface of a windshield glass including this sensing surface is subjected to a treatment having a water-repellent (hydrophilic) effect (such as coating) and where the surface of the windshield glass is coated to have a higher (lower) surface tension than an uncoated glass.

In the vehicular wiper controlling apparatus according to the present invention, it is preferable that the pattern data storing part further stores displacement status pattern data representing a displacement status of the output signal of the photo-detector when a human hand contacts the sensing surface.

In the vehicular wiper controlling apparatus according to the present invention, it is preferable that the pattern data storing part further stores displacement status pattern data representing a displacement status of the output signal of the photo-detector when an oil film is lying on the sensing surface.

EFFECTS OF THE INVENTION

With the above-described configuration, the wiper controlling apparatus according to the present invention can monitor the condition of the sensing surface even during the wiper operation without masking the signal from the photo emission element. Thus, the condition of the sensing surface can be monitored constantly regardless of the operation status of the wiper. Accordingly, it is possible to provide a wiper controlling apparatus promptly responding to the change in the condition of the sensing surface.

BRIEF DESCRIPTION OF DRAWINGS

FIG. 9 shows a graph showing an output signal waveform (a) from a photo-detector when a raindrop impacts on a sensing surface and an upward displacement amount (b), a downward displacement amount (c), a successive upward displacement amount (d) and a successive downward displacement amount (e) that are generated based on a sampling data train obtained at a sampling period N (N=500 μsec).

FIG. 10 shows a graph showing an output signal waveform (a) from the photo-detector when running water from a vehicular roof passes over the sensing surface and an upward displacement amount (b), a downward displacement amount (c), a successive upward displacement amount (d) and a successive downward displacement amount (e) that are generated based on the sampling data train obtained at a sampling period N (N=500 μsec).

FIG. 11 shows a graph showing an output signal waveform (a) from the photo-detector when a finger contacts the sensing surface and an upward displacement amount (b), a downward displacement amount (c), a successive upward displacement amount (d) and a successive downward displacement amount (e) that are generated based on the sampling data train obtained at a sampling period N (N=500 μsec).

FIG. 12 shows a graph showing an output signal waveform (a) from the photo-detector when condensation forms on the sensing surface and an upward displacement amount (b), a downward displacement amount (c), a successive upward displacement amount (d) and a successive downward displacement amount (e) that are generated based on the sampling data train obtained at a sampling period N (N=500 μsec).

FIG. 13 shows a graph showing an output signal waveform (a) from the photo-detector when a wiper blade passes over the sensing surface and an upward displacement amount (b), a downward displacement amount (c), a successive upward displacement amount (d) and a successive downward displacement amount (e) that are generated based on the sampling data train obtained at a sampling period N (N=500 μsec).

FIG. 14 is a drawing for illustrating an example of status displacement patterns.

FIG. 15 is a graph showing an output signal waveform (a) from the photo-detector when a raindrop impacts on the sensing surface and an upward displacement amount (b), a downward displacement amount (c), a successive upward displacement amount (d) and a successive downward displacement amount (e) that are generated based on a sampling data train obtained at a sampling period 8N (i.e., 4 msec).

FIG. 16 is a graph showing an output signal waveform (a) from the photo-detector when a raindrop impacts on the sensing surface and an upward displacement amount (b), a downward displacement amount (c), a successive upward displacement amount (d) and a successive downward displacement amount (e) that are generated based on a sampling data train obtained at a sampling period 64N (i.e., 32 msec).

FIG. 17 is a graph showing an output signal waveform (a) from the photo-detector when a raindrop impacts on the sensing surface and an upward displacement amount (b), a downward displacement amount (c), a successive upward displacement amount (d) and a successive downward displacement amount (e) that are generated based on a sampling data train obtained at a sampling period 512N (i.e., 256 msec).

FIG. 18 is a drawing for illustrating status displacement patterns obtained by converting maximum values in FIG. 14 into values at seven levels.

FIG. 19 is a drawing for illustrating status displacement patterns obtained by converting maximum values in FIG. 14 into values at three levels.

FIG. 20($a$) illustrates an example of five kinds of the status displacement patterns, and FIG. 20($b$) illustrates an example of displacement status data obtained at the time of operation.

FIG. 21 is a drawing for showing difference values obtained from FIGS. 20($a$) and 20($b$).

FIG. 22 is a drawing for illustrating an example of displacement status patterns obtained respectively for water-repellent and hydrophilic properties.

DESCRIPTION OF THE INVENTION

Figure 1:
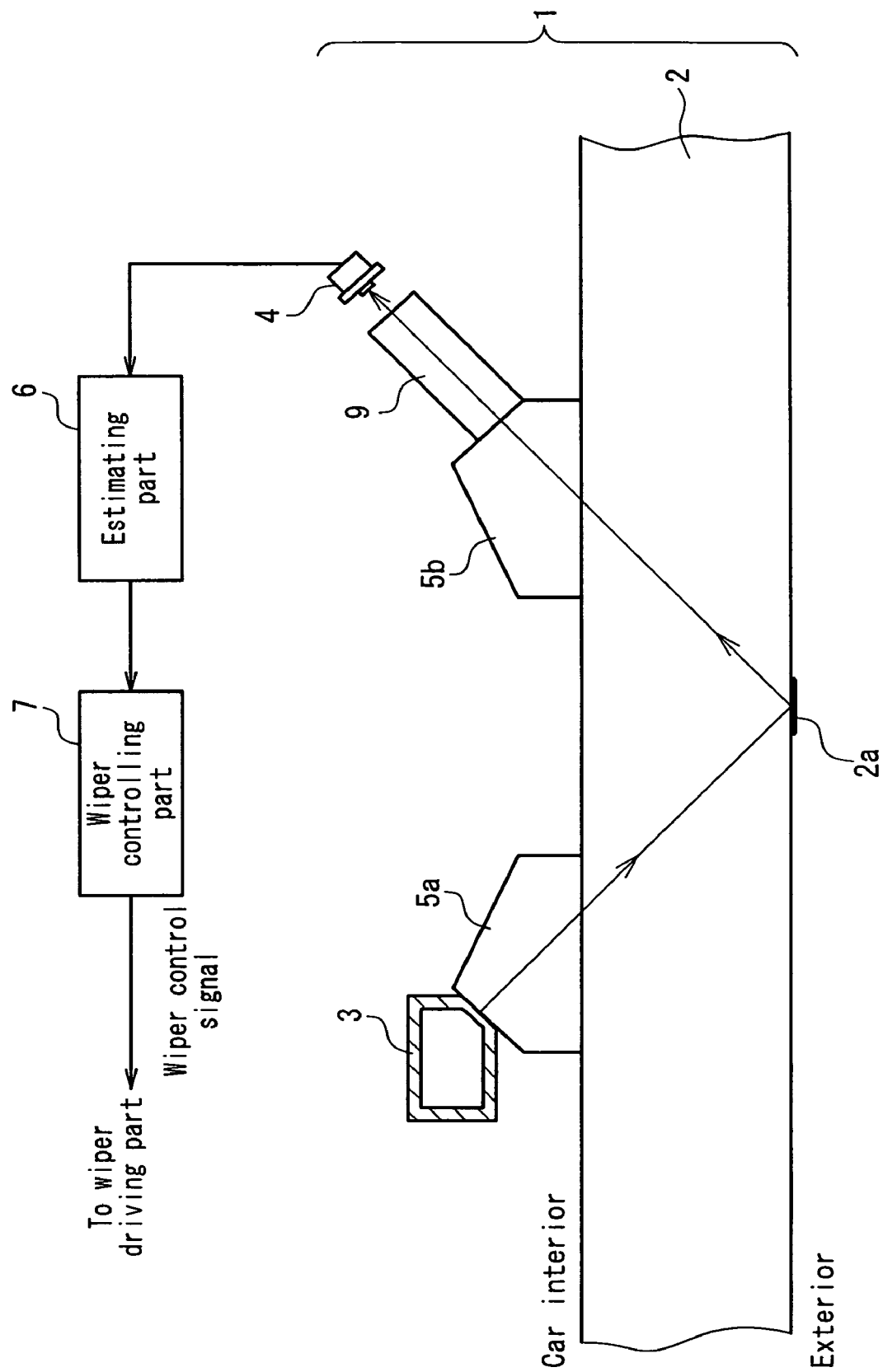
FIG. 1 is a block diagram showing a configuration of a wiper controlling apparatus according to an embodiment of the present invention, including a peripheral configuration.

The following is a detailed description of an embodiment of the present invention, with reference to the accompanying drawings. FIG. 1 is a block diagram showing a configuration of a wiper controlling apparatus according to an embodiment of the present invention, including a peripheral configuration.

As shown in FIG. 1, the wiper controlling apparatus according to the present embodiment includes an optical part 1 that outputs a signal representing an optical condition of a sensing surface 2$a$ provided on a vehicular windshield glass 2, an estimating part 6 that estimates an object lying on the sensing surface 2$a$ based on the output signal from the optical part 1, and a wiper controlling part 7 that outputs a wiper control signal according to the estimation result of the estimating part 6. The wiper control signal is sent from the wiper controlling part 7 to a motor for driving a wiper or the like, thereby controlling an operating speed, an operating interval, etc. of the wiper.

The optical part 1 is configured so that light emitted from a photo emission element 3 such as an LED travels through a prism glass 5$a$, is introduced in the windshield glass 2, is subjected to a total reflection on the sensing surface 2$a$ set on part of an external surface of this vehicle, travels through a prism glass 5$b$ and reaches a photo-detector 4 such as a photodiode (PD). It is preferable to turn the light emitted from the photo emission element 3 to parallel light using a lens or the like (not shown). Also, it is preferable to use a lens 9 so that the light reaching the photo-detector 4 is focused on a light receiving surface of the photodetector 4. Incidentally, the optical part 1 shown in FIG. 1 is configured so that the light from the photo emission element 3 is subjected to several times of the total reflection in the prism glasses 5$a$ and 5$b$ and the windshield glass 2.

In the optical part 1, the positions of individual elements including the photo emission element 3, the sensing surface 2$a$ and the photo-detector 4 are adjusted so that an output of the photo-detector 4 becomes maximal in the case where a water droplet or the like is not lying on the sensing surface 2$a$. When the water droplet or the like impacts on the sensing surface 2$a$, the total reflection condition on the sensing surface 2$a$ is disturbed. Thus, at least part of the light irradiated from the photo emission element 3 to the sensing surface 2$a$ passes and comes out of the vehicle without being subjected to the total reflection on the sensing surface 2$a$, so that the output of the photo-detector 4 drops. Accordingly, by analyzing the change in the output signal of the photo-detector 4 in the estimating part 6, the impact of water or the like on the sensing surface 2$a$ is estimated.

Unlike the conventional vehicular wiper controlling apparatus, the vehicular wiper controlling apparatus according to the present embodiment does not mask the output signal from the photo-detector 4. In other words, the conventional vehicular wiper controlling apparatus masks the output signal from the photo-detector 4 during a period in which the wiper operation signal is ON or during a specific period within that ON period, and does not carry out a processing of estimating a lying object during this period as described above. In contrast, in the vehicular wiper controlling apparatus according to the present embodiment, the estimating part 6 utilizes the output signal from the photo-detector 4 over the entire period without masking it. Also, the vehicular wiper controlling apparatus according to the present embodiment can discriminate between a change in the output signal of the photo-detector 4 at the time of the passage of a wiper blade over the sensing surface 2$a$ and a change in the output signal of the photo-detector 4 when a raindrop or the like impacts on the sensing surface 2$a$. In the following, a detailed example of a configuration for achieving this function will be described, with reference to the accompanying drawings.

Figure 2:
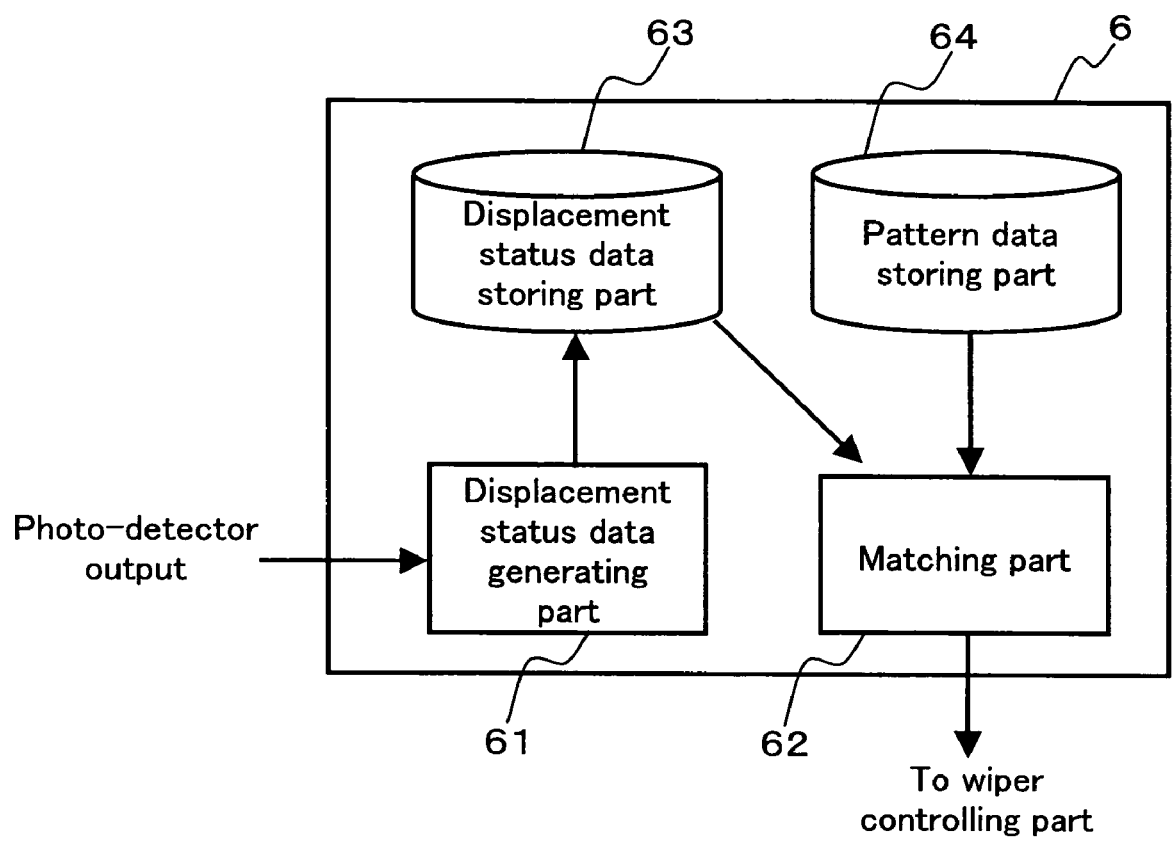
FIG. 2 is a block diagram showing a schematic configuration of an estimating part in a vehicular wiper controlling apparatus according to the present embodiment.

FIG. 2 is a block diagram showing a schematic configuration of the estimating part 6 in the vehicular wiper controlling apparatus according to the present embodiment. As shown in FIG. 2, the estimating part 6 includes a displacement status data generating part 61, a matching part 62, a displacement status data storing part 63 and a pattern data storing part 64.

The displacement status data generating part 61 inputs the output signal from the photo-detector 4 and both samples this output signal at plural kinds of sampling periods and calculates the difference between two sampled values that are successive in terms of time. The result of calculation is stored temporarily in the displacement status data storing part 63 as displacement status data representing the calculation result at each sampling period.

Figure 3:
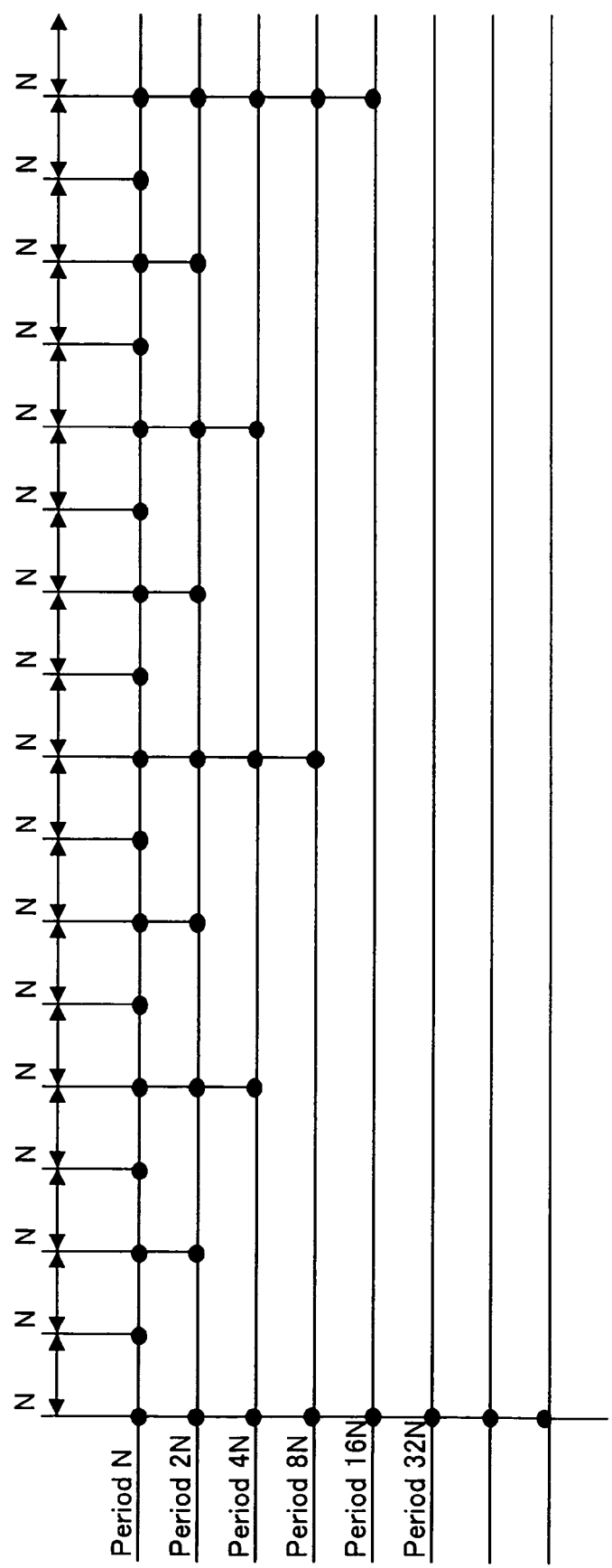
FIG. 3 is a timing chart showing sampling timings of a displacement status data generating part.

Now, referring to FIG. 3, the processing of generating the displacement status data by the displacement status data generating part 61 will be described. FIG. 3 shows sampling timings of the displacement status data generating part 61. As shown in FIG. 3, the displacement status data generating part 61 performs sampling at period N, for example. In the present embodiment, a data sampling period necessary for a single processing of estimating the condition of the sensing surface 2a performed by the estimating part 6 is 512N. In other words, the estimating part 6 generates a plurality of sampling data trains from the data that have been sampled at period N from the output signal of the photo-detector 4 and estimates the condition of the sensing surface 2a based on the generated plurality of sampling data trains.

The displacement status data generating part 61 generates the displacement status data representing the displacement status of the output signal of the photo-detector 4 based on each of the plurality of sampling data trains obtained at the plurality of kinds of periods such as N, 2N, 4N . . . .

As the above-mentioned plurality of sampling data trains, the displacement status data generating part 61 preferably generates a sampling data train consisting of m sampling data (where $m=2^{a \times b}$, with a and b being an integer) obtained at a predetermined clock period N and a sampling data train consisting of $(2^b+1), \ldots, ((m/2^{a \times c})+1)$ sampling data obtained at clock periods obtained by multiplying the clock period N respectively by $2^a, \ldots, 2^{a \times c}$ (where c is an integer from 1 to b).

For example, in the case where the data sampling period necessary for the single processing of estimating the condition of the sensing surface 2a performed by the estimating part 6 is 512N as in the present embodiment, the displacement status data generating part 61 generates four kinds of sampling data trains in total, namely, a sampling data train consisting of 513 sampling data obtained at period N, a sampling data train consisting of 65 sampling data obtained at period 8N, a sampling data train consisting of 9 sampling data obtained at period 64N and a sampling data train consisting of 2 sampling data obtained at period 512N, for example. Alternatively, other than this example, five kinds of sampling data trains in total obtained respectively at periods N, 4N, 16N, 64N and 256N may be generated.

It should be noted that the length of a sampling period N serving as a basis (a base sampling period) and the length of the data sampling period necessary for the single processing of estimating the condition of the sensing surface 2a performed by the estimating part 6 may be set freely according to an accuracy required for the wiper controlling apparatus, etc. It is conceivable to set the period N to 500 μsec, for example, though an embodiment of the present invention is not limited to this.

Examples of the displacement status data generated by the displacement status data generating part 61 can include:

(1) the displacement amounts of the sampling data respectively in the above-noted plurality of sampling data trains;

(2) the difference between the displacement amounts of the sampling data respectively in the above-noted plurality of sampling data trains;

(3) the successive displacement amounts representing an amount that the sampling data are displaced successively in either an upward direction or a downward direction respectively in the above-noted plurality of sampling data trains; and (4) the number of the successive displacements representing the number of times that the sampling data are displaced successively in either the upward direction or the downward direction respectively in the above-noted plurality of sampling data trains.

Incidentally, it is preferable that (1) and (2) described above are generated as displacement status data that are classified further as follows in order to avoid the complexity of handling negative data.

(1-a) the upward displacement amounts of the sampling data respectively in the above-noted plurality of sampling data trains;

(1-b) the downward displacement amounts of the sampling data respectively in the above-noted plurality of sampling data trains;

(2-a) the difference between the upward displacement amounts (the increase) of the sampling data respectively in the above-noted plurality of sampling data trains;

(2-b) the difference between the upward displacement amounts (the decrease) of the sampling data respectively in the above-noted plurality of sampling data trains;

(2-c) the difference between the downward displacement amounts (the increase) of the sampling data respectively in the above-noted plurality of sampling data trains; and (2-d) the difference between the downward displacement amounts (the decrease) of the sampling data respectively in the above-noted plurality of sampling data trains.

Further, it is preferable that (3) and (4) described above are classified according to whether the successive displacement direction is the upward direction or the downward direction and then generated as displacement status data as follows:

(3-a) the successive upward displacement amounts representing an amount that the sampling data are displaced successively in the upward direction respectively in the above-noted plurality of sampling data trains;

(3-b) the successive downward displacement amounts representing an amount that the sampling data are displaced successively in the downward direction respectively in the above-noted plurality of sampling data trains;

(4-a) the number of the successive upward displacements representing the number of times that the sampling data are displaced successively in the upward direction respectively in the above-noted plurality of sampling data trains; and (4-b) the number of the successive downward displacements representing the number of times that the sampling data are displaced successively in the downward direction respectively in the above-noted plurality of sampling data trains.

From each of these data (1) to (4) or the (1-a) to (4-b), a fluctuation component with respect to a plurality of sampling times is determined. In other words, it is considered that viscosity changes, etc. of a lying object and a contact object can be estimated from this fluctuation component. For example, a raindrop is considered to have a substantially constant inertia due to buoyancy. In the case where this raindrop impacts on a glass surface, the change in the shape of the raindrop caused by the impact depends on the viscosity thereof. It should be noted that, even with the raindrops having the same viscosity, the degrees of the change in their shape differ if they have different inertias. In order to judge this degree of the change in shape reliably from the output (voltage change) amount of the sensor, the sensitivity of the sensing surface has to be constant. However, it is impossible in terms of both technology and cost to achieve parallel light with a constant flux density in the optical part of the vehicular wiper controlling apparatus. Thus, in the vehicular wiper controlling apparatus according to the present embodiment, by judging the degree of the change in shape of an object such as a raindrop lying on the sensing surface 2a from the change in the output amount of the photo-detector 4 along a time axis, it is possible to discriminate between the conditions of water impact (a raindrop, running water, condensation, etc.) on the windshield 2 occurring in a general situation. Also, from the change in the output amount of the photo-detector 4 along the time axis, it is possible to discriminate between the kinds of various lying objects or contact objects on the sensing surface 2a other than such lying water.

Figure 4:
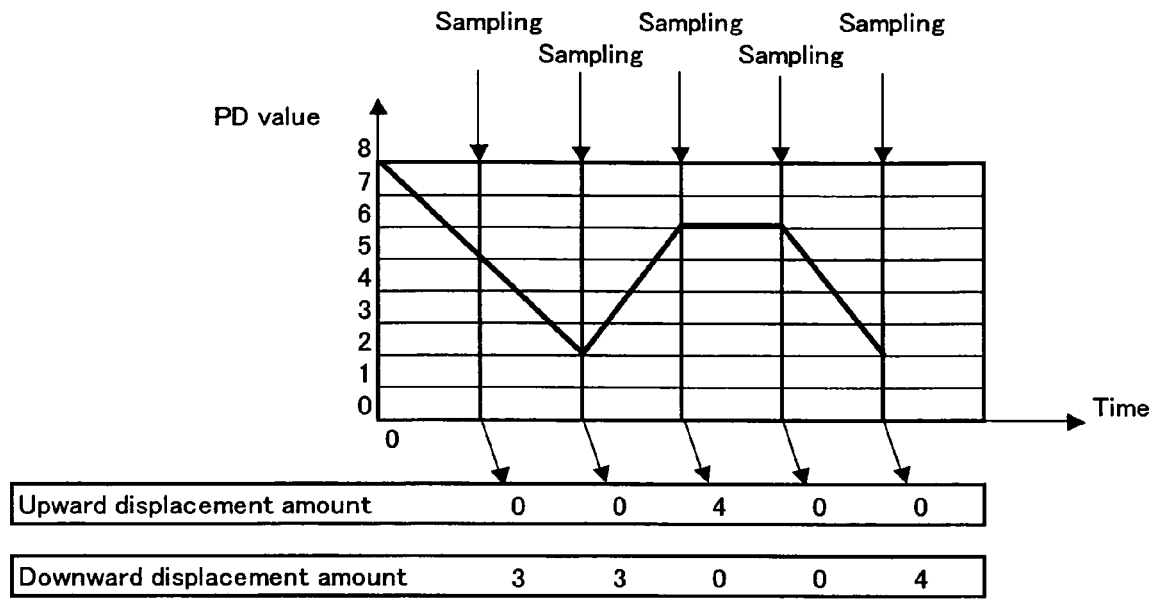
FIG. 4 is a drawing for illustrating examples of calculating an upward displacement amount and a downward displacement amount.

Herein, FIG. 4 illustrates examples of calculating the upward displacement amount (1-a) and the downward displacement amount (1-b) described above. As shown in FIG. 4, with respect to two successive sampling data $S_i$, $S_{i+1}$ (assuming that they are sampled in this order) in the sampling data train, if $S_i \leq S_{i+1}$, the value of $S_{i+1} - S_i$ is the upward displacement amount at the sampling timing $S_{i+1}$. If $S_i \geq S_{i+1}$, the value of the upward displacement amount at the sampling timing $S_{i+1}$ is 0. Similarly, with respect to two successive sampling data $S_i$, $S_{i+1}$ (assuming that they are sampled in this order) in the sampling data train, if $S_i > S_{i+1}$, the value of $S_i - S_{i+1}$ is the downward displacement amount at the sampling timing $S_{i+1}$. If $S_i \leq S_{i+1}$, the value of the downward displacement amount at the sampling timing $S_{i+1}$ is 0.

Figure 5:
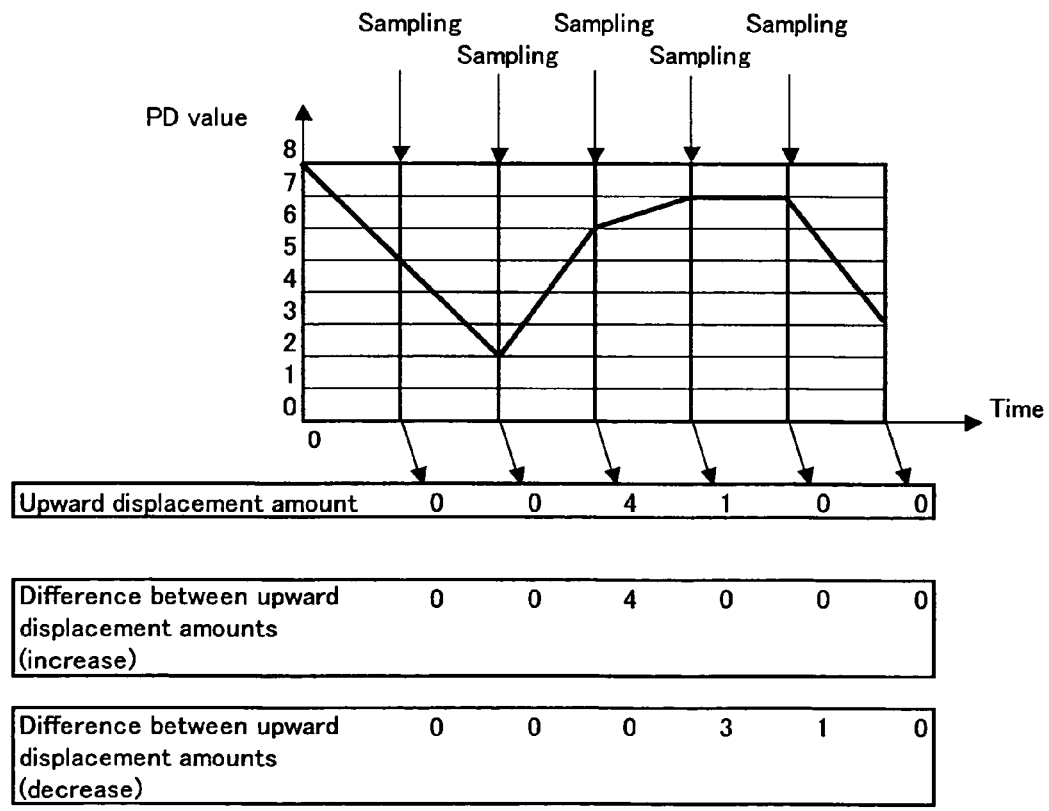
FIG. 5 shows examples of calculating a difference between upward displacement amounts (an increase) (2-a) and a difference between upward displacement amounts (a decrease) (2-b) mentioned above.

FIG. 5 shows examples of calculating the difference between upward displacement amounts (the increase) (2-a) and the difference between upward displacement amounts (the decrease) (2-b) mentioned above. As shown in FIG. 5, the difference between the upward displacement amounts (the increase) and the difference between the upward displacement amounts (the decrease) are obtained from the upward displacement amounts (1-a) described above. With respect to upward displacement amounts $U_i$, $U_{i+1}$ for the two successive sampling data $S_i$, $S_{i+1}$ (assuming that they are sampled in this order) in the sampling data train, if $U_i < U_{i+1}$, the difference between the upward displacement amounts (the increase) is $U_{i+1} - U_i$ and the difference between the upward displacement amounts (the decrease) is 0 at the sampling timing $S_{i+1}$. If $U_i > U_{i+1}$, the difference between the upward displacement amounts (the increase) is 0 and the difference between the upward displacement amounts (the decrease) is $U_i - U_{i+1}$ at the sampling timing $S_{i+1}$. Incidentally, if $U_i = U_{i+1}$, both of the difference between the upward displacement amounts (the increase) and the difference between the upward displacement amounts (the decrease) are 0.

Figure 6:
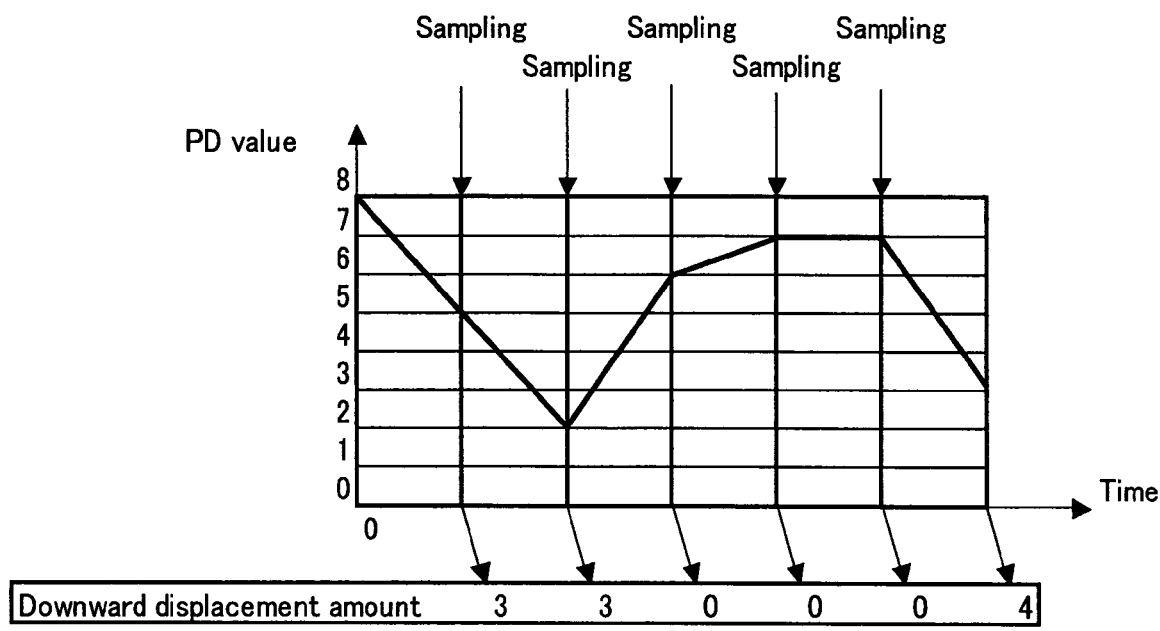
FIG. 6 shows examples of calculating a difference between downward displacement amounts (an increase) (2-c) and a difference between downward displacement amounts (a decrease) (2-d) mentioned above.

FIG. 6 shows examples of calculating the difference between downward displacement amounts (the increase) (2%) and the difference between the downward displacement amounts (the decrease) (2-d) mentioned above. As shown in FIG. 6, the difference between the downward displacement amounts (the increase) and the difference between the downward displacement amounts (the decrease) are obtained from the downward displacement amounts (1-b) described above. With respect to downward displacement amounts $D_i$, $D_{i+1}$ for the two successive sampling data $S_i$, $S_{i+1}$ (assuming that they are sampled in this order) in the sampling data train, if $D_i < D_{i+1}$, the difference between the downward displacement amounts (the increase) is $D_{i+1} - D_i$ and the difference between the downward displacement amounts (the decrease) is 0 at the sampling timing $S_{i+1}$. If $D_i > D_{i+1}$, the difference between the downward displacement amounts (the increase) is 0 and the difference between the downward displacement amounts (the decrease) is $D_i - D_{i+1}$ at the sampling timing $S_{i+1}$. Incidentally, if $D_i = D_{i+1}$, both of the difference between the downward displacement amounts (the increase) and the difference between the downward displacement amounts (the decrease) are 0.

Figure 7:
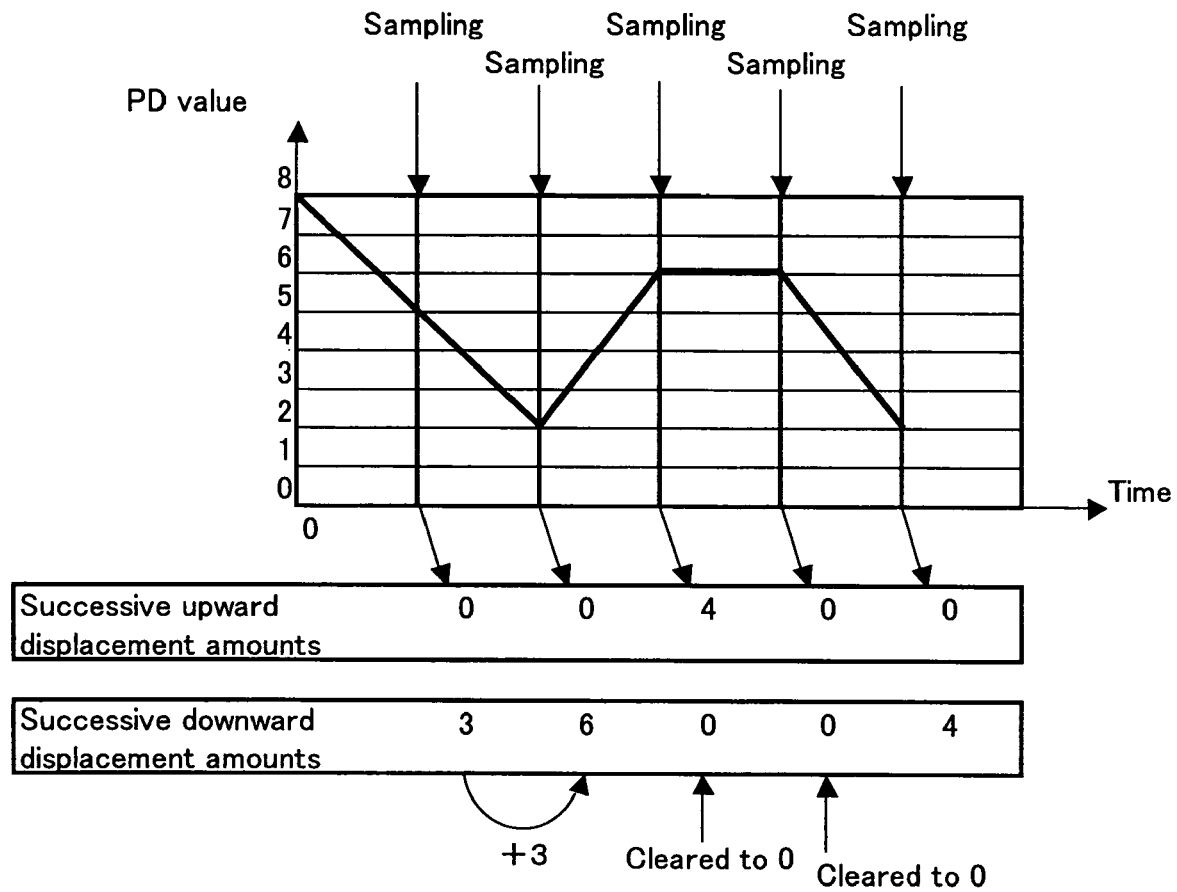
FIG. 7 shows examples of calculating successive upward displacement amounts (3-a) and successive downward displacement amounts (3-b) mentioned above.

FIG. 7 shows examples of calculating the successive upward displacement amounts (3-a) and the successive downward displacement amounts (3-b) mentioned above. As shown in FIG. 7, when the sampling data decrease successively in the sampling data train, the value obtained by adding a current downward displacement amount to the previous successive downward displacement amount serves as the successive downward displacement amount. When the displacement of the sampling data changes from downward to upward or the displacement is 0, the successive downward displacement amount is cleared to 0 as shown in FIG. 7. Also, when the sampling data increase successively in the sampling data train, the value obtained by adding a current upward displacement amount to the previous successive upward displacement amount serves as the successive upward displacement amount. When the displacement of the sampling data changes from upward to downward or the displacement is 0, the successive upward displacement amount is cleared to 0.

Figure 8:
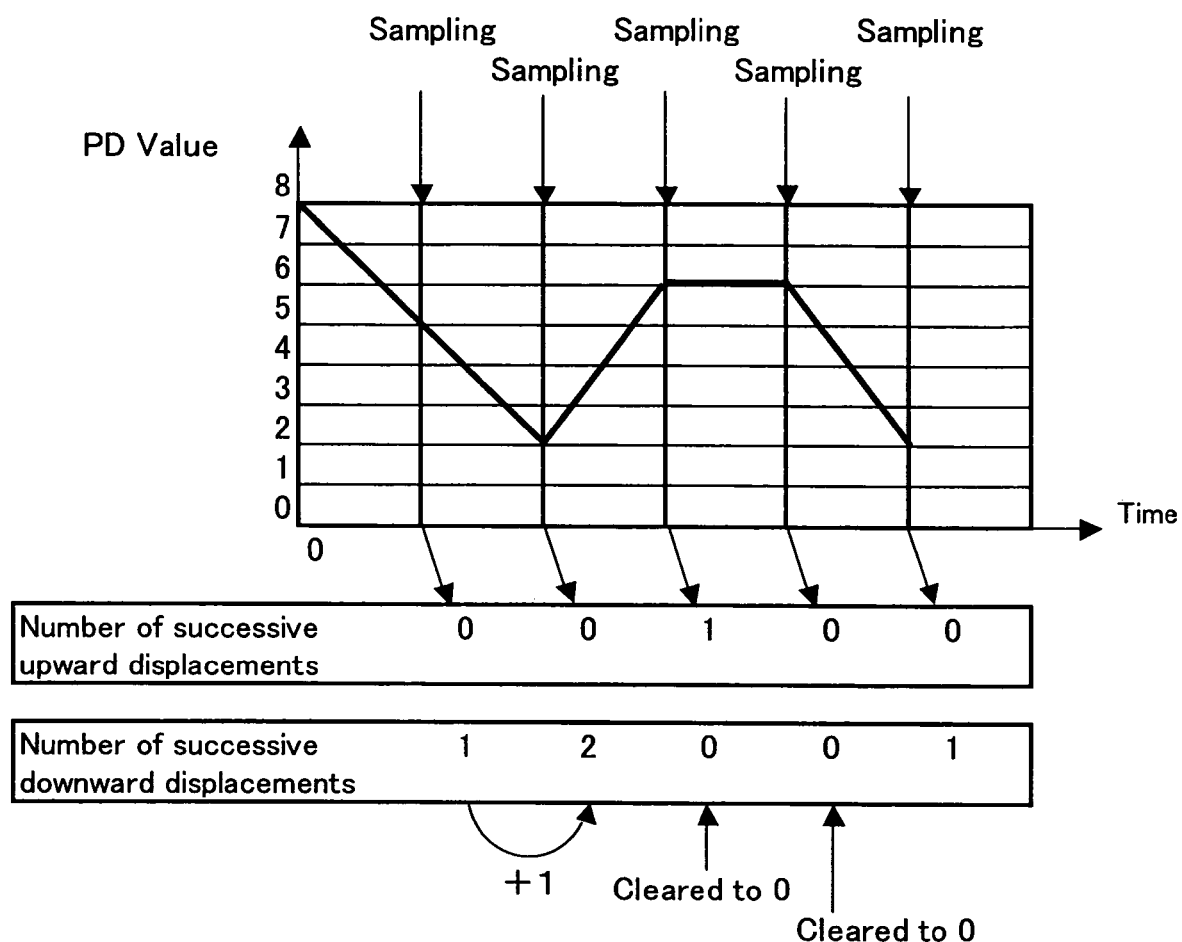
FIG. 8 shows examples of calculating the number of successive upward displacements (4-a) and the number of successive downward displacements (4-b) mentioned above.

FIG. 8 shows examples of calculating the number of successive upward displacements (4-a) and the number of successive downward displacements (4-b) mentioned above. As shown in FIG. 8, when the sampling data decrease successively in the sampling data train, the value obtained by adding 1 to the previous number of successive downward displacements serves as the number of successive downward displacements. When the displacement of the sampling data changes from downward to upward or the displacement is 0, the number of successive downward displacements is cleared to 0 as shown in FIG. 8. Also, when the sampling data increase successively in the sampling data train, the value obtained by adding 1 to the previous number of successive upward displacements serves as the number of successive upward displacements. When the displacement of the sampling data changes from upward to downward or the displacement is 0, the number of successive upward displacements is cleared to 0.

The displacement status data generating part 61 stores in the displacement status data storing part 63 the displacement status data that are generated individually from a plurality of sampling data trains with different sampling periods as described above. The displacement status data to be stored in the displacement status data storing part 63 may be the displacement status data themselves generated in the displacement status data generating part 61. However, in order to save a storage capacity of the displacement status data storing part 63, the displacement status data generating part 61 may calculate a feature value of the displacement status data generated from the plurality of sampling data trains, and the calculated feature value may be stored. The feature value can be, for example, a maximum value of the displacement status data generated from each of the sampling data trains or a value obtained by expressing this maximum value further by a value at predetermined levels. Also, not only the maximum value but also an average, a sum, a difference, etc. of the displacement status data can be used as the feature value.

The matching part 62 compares the displacement status data that have been generated in the displacement status data generating part 61 and stored in the displacement status data storing part 63 as described above and displacement status patterns that have been stored in advance in the pattern data storing part 64, thus estimating the condition of the sensing surface 2a.

The pattern data storing part 64 stores displacement status patterns according to various modes of an object lying on the sensing surface 2a (for example, a raindrop, running water, condensation, etc.) and displacement status patterns caused by a contact object other than the lying object (including a passing object). The displacement status patterns caused by the contact object are, for example, a displacement status pattern when a wiper blade passes over the sensing surface and a displacement status pattern when a human finger contacts the sensing surface. Incidentally, the case where the "finger contacts the sensing surface" assumes that a finger or the like contacts the sensing surface at the time of cleaning a window glass at a gas station or the like. The condensation also includes a condition in which drizzle impacts on the sensing surface, as well as condensation.

These displacement status patterns can be calculated by completely the same method as the displacement status data described above based on an output signal of the photo-detector 4 when reproducing experimentally the condition in which the lying object or the contact object described above is present on the sensing surface 2a and, in this state, irradiating light from the photo emission element 3 to the sensing surface 2a. In other words, similarly to the displacement status data, the displacement status pattern also is generated from the sampling data trains obtained in the sampling periods different from each other.

Incidentally, at the time of implementing the wiper controlling apparatus according to the present invention, it is not always necessary to use all of the displacement status data illustrated in (1-a) to (4-b) above, and some other displacement status data may be used. In other words, the wiper controlling apparatus related to the implementation of the present invention does not have to store all of the displacement status patterns to be compared with the displacement status data illustrated in (1-a) to (4-b) above. For example, even in the case of using any one kind of the displacement status data illustrated in (1-a) to (4-b) above, it is possible to estimate how the object is lying on the sensing surface 2a or whether the contact object (including the passing object such as a wiper blade or the like) is present on the sensing surface 2a by generating the above-noted displacement status data respectively from the plurality of sampling data trains obtained in plural kinds of sampling periods and comparing them with the displacement status patterns that have been calculated in advance in a similar manner. However, in the case where a higher estimation accuracy is required, it is preferable to use a largest possible number of kinds of the displacement status data as illustrated in (1-a) to (4-b) above.

The following description is directed to the principle in which, in the vehicular wiper controlling apparatus of the present embodiment, the condition of the sensing surface 2a can be estimated based on the displacement status data generated from the plurality of sampling data trains obtained in the plural kinds of sampling periods.

First, the relationship between the form of water impacting on the sensing surface 2a and the output of the photo-detector 4 will be described. For example, comparison will be made between a large raindrop and a drizzle drop. When a large raindrop impacts on the sensing surface 2a, a substantial area of the sensing surface 2a is covered with the raindrop, so that the output of the photo-detector 4 decreases considerably. Further, since the raindrop after the impact has a large kinetic energy, it continues to jiggle over a substantial period of time after it impacts on the sensing surface 2a. While a large raindrop is jiggling on the sensing surface 2a, the output of the photo-detector 4 also repeats rising and falling and thus fluctuates. On the other hand, when a very small raindrop such as a drizzle drop impacts on the sensing surface 2a, only a small area of the sensing surface 2a is covered, so that the output of the photo-detector 4 does not fall very much. Further, since the drizzle drop after the impact has a small kinetic energy, it stops jiggling soon after the impact. Consequently, the output of the photo-detector 4 stabilizes shortly.

As described above, the difference in the form of the impacting water is reflected on the movement of the water after its impact on the sensing surface 2a. Then, in correspondence with the movement of the water that has impacted, the output of the photo-detector 4 after the impact also varies. This applies not only to water but also various materials that may impact on or contact the sensing surface 2a. In other words, the inventors of the present invention found that the variation in the output of the photo-detector 4 after something impacted on the sensing surface 2a or while something was in contact therewith had an intrinsic displacement pattern according to a physical property of the lying object or the contact object. On this principle, by analyzing the variation, namely, the "fluctuation" of the output of the photo-detector 4 after water or the like impacts on the sensing surface 2a or while it is in contact therewith, it is possible to determine the form, etc. of the object lying on or contacting the sensing surface 2a.

Now, the following is a specific example of the displacement status patterns stored in advance in the pattern data storing part 64 of the wiper controlling apparatus according to the present embodiment. Here, five kinds of conditions on the sensing surface 2a (raindrop impact, running water passage, finger contact, condensation formation and wiper blade passage) were reproduced experimentally, and four kinds of sampling data trains at sampling periods of N, 8N, 64N and 512N were obtained from the output signals from the photo-detector 4 in the respective conditions. N was set to be 500 μsec. Then, from these sampling data trains, displacement status patterns were obtained for four kinds of the displacement status data, i.e., the upward displacement amount (1-a), the downward displacement amount (1-b), the successive upward displacement amount (3-a) and the successive downward displacement amount (3-b).

FIGS. 9 to 13 show output signal waveforms ((a) in each figure) from the photo-detector 4 when a raindrop impacts on the sensing surface 2a (FIG. 9), when running water from a vehicular roof passes over the sensing surface 2a (FIG. 10), when a finger contacts the sensing surface 2a (FIG. 11), when condensation forms on the sensing surface 2a (FIG. 12) and when a wiper blade passes over the sensing surface 2a (FIG. 13), respectively, and upward displacement amounts ((b) in each figure), downward displacement amounts ((c) in each figure), successive upward displacement amounts ((d) in each figure) and successive downward displacement amounts ((e) in each figure) that are generated based on sampling data trains obtained from the respective output signals at a sampling period N (N=500 μsec). In each of FIGS. 9 to 13, the vertical axis indicates the output of the photo-detector 4 (unit: dot), whereas the horizontal axis indicates the time elapsed from the start of sampling (unit: 500 μsec). It is noted that 1 dot serving as the unit of the vertical axis indicates the unit of 1 resolution of an A/D converter inside a microcomputer constituting the displacement status data generating part 61. In addition, the signal indicated by solid and broken lines in FIG. 13 is a wiper operation signal representing whether or not the wiper is in operation. When this signal is at a high level, the wiper is in operation. When it is at a low level, the wiper is at a halt.

In this example, the maximum values of the individual displacement amounts at the time of the raindrop impact obtained as shown in FIG. 9 are calculated as feature values of these displacement amounts, and further converted into values at predetermined levels. Thus, the displacement status data generating part 61 in the wiper controlling apparatus using the displacement status pattern described here only has to calculate the maximum values of the individual displacement amounts obtained as the displacement status data as feature values of these displacement amounts and further calculate values by converting them into the above-noted values at predetermined levels similarly to the above, thus storing the values in the displacement status data storing part 63.

For example, the maximum value of the upward displacement amount shown in FIG. 9(b) was 33, that of the downward displacement amount shown in FIG. 9(c) was 36, that of the successive upward displacement amount shown in FIG. 9(d) was 34, and that of the successive downward displacement amount shown in FIG. 9(e) was 36. Similarly, the maximum values of the individual displacement amounts at the time of passage of the running water shown in FIGS. 10(b) to (e), the maximum values of the individual displacement amounts at the time of the finger contact shown in FIGS. 11(b) to (e), the maximum values of the individual displacement amounts at the time of formation of the condensation shown in FIGS. 12(b) to (e) and the maximum values of the individual displacement amounts at the time of passage of the wiper blade shown in FIGS. 13(b) to (e) were calculated respectively. The section d(N) in FIG. 14 shows the results thereof.

FIGS. 15 to 17 show upward displacement amounts ((b) in each figure), downward displacement amounts ((c) in each figure), successive upward displacement amounts ((d) in each figure) and successive downward displacement amounts ((e) in each figure) that are generated based on the sampling data trains obtained from the output signals at the time of raindrop impact shown in FIG. 9(a) at sampling periods of 8N (i.e., 4 msec), 64N (i.e., 32 msec) and 512N (i.e., 256 msec). Based on them, the maximum values of the respective displacement amounts in the case where the condition of the sensing surface 2a corresponds to the "raindrop impact" are obtained as in sections d(8N), d(64N) and d(512N) in FIG. 14.

Further, the sections d(8N), d(64N) and d(512N) in FIG. 14 show the maximum values of the respective displacement amounts that were generated based on the sampling data trains obtained in the respective cases where the condition of the sensing surface 2a corresponded to the running water passage, the finger contact, the condensation formation and the wiper blade passage at sampling periods of 8N, 64N and 512N, though not shown in the figure.

Once the various conditions of the sensing surface 2a were reproduced experimentally and the maximum values of the individual displacement amounts shown in FIG. 14 were calculated as described above, then these maximum values were converted into values at predetermined levels for each of the conditions of the sensing surface 2a. For instance, in the example illustrated by FIG. 18, the maximum values were converted into values at seven levels. Also, in the example illustrated by FIG. 19, the maximum values were converted into values at three levels. Incidentally, FIGS. 18 and 19 indicate the individual level values by signs to facilitate the understanding of the description. However, actual level values are expressed by numerical values or the like and stored in the pattern data storing part 64 as the displacement status patterns.

As becomes clear from FIGS. 9 to 19, in each of the cases where the condition of the sensing surface 2a corresponded to the raindrop impact, the running water passage, the finger contact, the condensation formation and the wiper blade passage, the mode of the sampling data trains obtained at the plural kinds of sampling periods and the displacement status patterns formed of the maximum values of the individual displacement amounts are different from each other remarkably.

For example, the output of the photo-detector 4 changes more slowly when the wiper blade passes than when the raindrop impacts. Thus, in the displacement status pattern obtained in a short sampling period, the displacement amount at the time of the wiper blade passage is smaller than the displacement amount at the time of the raindrop impact. The output of the photo-detector 4 at the time of the wiper blade passage decreases by the passage of a bulge of water gathered by the wiper blade over the sensing surface 2a. After the wiper blade passes, water does not remain on the sensing surface 2a, so that the output recovers instantly. Accordingly, the displacement status pattern in the case of the wiper blade passage shows large displacement amounts in both of the downward direction and the upward direction.

Thus, in accordance with the present embodiment, it is possible to identify the impact of water such as a raindrop on the sensing surface 2a or the passage of the wiper blade based on the output signal of the photo-detector 4 using the above-described displacement status patterns. Therefore, unlike the conventional case, the output signal of the photo-detector does not have to be masked while the wiper is in operation. Regardless of whether or not the wiper is in operation, the condition of the sensing surface 2a can be estimated throughout the entire period. This allows a wiper operation control to respond rapidly to the change in the condition of the sensing surface 2a.

Now, an exemplary processing of the matching part 62 will be described specifically, with reference to FIGS. 20 and 21.

Here, five kinds of patterns shown in FIG. 20(a) (i.e., at the times of the raindrop impact, the wiper passage, the running water passage, the finger contact and the condensation formation) for the condition of the sensing surface are stored in advance in the pattern data storing part 64 as the displacement status patterns. When the wiper controlling apparatus of the present embodiment is operated, the displacement status data shown in FIG. 20(b) are obtained by the displacement status data generating part 61 and stored in the displacement status data storing part 63.

The matching part 62 reads out the displacement status data in FIG. 20(b) from the displacement status data storing part 63 and compares them with the displacement status patterns of FIG. 20(a) stored in the pattern data storing part 64. Here, for each of the various kinds of the displacement status data (the upward displacement amount, the downward displacement amount, the upward successive displacement amount, the downward successive displacement amount, . . . ) in each of the conditions of the sensing surface, the matching part 62 calculates the difference between a value of the displacement status data and a value of the displacement status pattern.

FIG. 21 shows values of the difference calculated from the FIGS. 20(a) and 20(b).

For each of the conditions of the sensing surface, the matching part 62 further calculates the sum of the differences calculated as shown in FIG. 21. Then, a coincidence order is determined in increasing order of the sum of the differences. According to the results shown in FIG. 21, the matching part 62 estimates that the condition of the sensing surface 2a at this time is a condition where a raindrop is lying on the sensing surface 2a.

By the above processing, the matching part 62 compares the displacement status data that are generated by the displacement status data generating part 61 with the displacement status patterns that have been obtained experimentally and stored in advance in the pattern data storing part 64, thereby estimating the condition of the sensing surface 2a.

Incidentally, the example illustrated above has been directed to the configuration in which the displacement status patterns of five kinds (at the times of the raindrop impact, the wiper passage, the running water passage, the finger contact and the condensation formation) for the condition of the sensing surface 2a are stored in advance in the pattern data storing part 64. However, the displacement status patterns are not limited to them alone. For example, it also is effective to store different displacement status patterns in advance depending on whether the sensing surface 2a is water repellent or hydrophilic. The reason follows.

A water-repellent treatment sometimes is carried out by coating a surface of a vehicular windshield with a water repellent, thus preparing a water-repellent glass. In this case, the movement of a raindrop impacting on the sensing surface is different from that on a usual glass (a glass that is not subjected to the water-repellent treatment). For example, the area in which a raindrop contacts the water-repellent glass is smaller than that in which a raindrop with the same mass contacts the usual glass. Further, since the raindrop lying on the water-repellent glass is moved on the sensing surface easily by wind pressure or the like, such a movement also changes the signal from the photo-detector. Moreover, when the raindrop is wiped off using the wiper, it turns into a thin water film on the glass surface immediately thereafter. Then, due to the water repellency of the glass surface, this water film turns into small water droplets. In this case, the signal from the photo-detector also is different from that in the usual case. Therefore, it is necessary to employ different control logics between the cases of the water-repellent glass and the usual glass.

However, the effect of the water-repellent treatment does not last semipermanently but diminishes with the wiping of the glass surface using the wiper blade. Thus, in practice, the control logic needs to be shifted to the control logic for the usual glass with the reduction of the water-repellent effect. However, it is difficult to control the shift timing. Also, it is not realistic to make a driver decide whether or not the windshield is treated to be water repellent in order to determine which control logic is to be employed. This is because the setting is troublesome and the driver might forget to make the setting. An automatic car wash sometimes washes a car using a treatment agent with a water repellency. In this case, regardless of the driver's awareness, the windshield surface including the sensing surface becomes water repellent. Thus, in the case where the windshield is treated to be water repellent, it conventionally has been difficult to estimate the condition of the sensing surface correctly.

In contrast, with the vehicular wiper controlling apparatus according to the present embodiment, the displacement status patterns for each of the case where the windshield is water repellent (treated to be water repellent) and the case where it is hydrophilic (treated to remove an oil film) only have to be stored in advance in the pattern data storing part 64. The condition of the sensing surface can be estimated accurately in either case where the windshield is water repellent or hydrophilic as described above because the displacement status data of the various kinds generated from the sampling data trains obtained at the plural kinds of sampling periods have feature values remarkably different from each other according to whether the sensing surface 2a is water repellent or hydrophilic as shown in FIG. 22 even if the conditions of the sensing surface, for example, the raindrop impact or the wiper passage are similar to each other.

As described above, the estimating part 6 in the vehicular wiper controlling apparatus according to the present embodiment has the pattern data storing part 64 that stores in advance the displacement status patterns representing displacement status of the output signal of the photo-detector 4 obtained in the case where a typical object lies on or contacts the sensing surface. Then, the matching part 62 compares the displacement status data obtained from the above-noted output signal within a predetermined sampling period with the above-noted displacement status patterns, thereby estimating the condition of the sensing surface 2a, namely, whether any object is lying on or contacts the sensing surface 2a (including any object passing over the sensing surface) within that sampling period. Since this configuration makes it possible to estimate that the wiper blade passes over the sensing surface 2a by identifying the wiper blade passage or a lying object such as a raindrop and other contact objects, the signal from the photo-detector does not need to be masked any longer even during the wiper operation. Accordingly, the impact of a raindrop, etc. can be detected over the entire period regardless of whether or not the wiper is in operation. Thus, even in the case where a vehicle is exposed to a heavy rain near the exit of a tunnel, it is possible to perform an appropriate wiper control promptly responding to the change in the condition of the sensing surface.

The wiper controlling part 7 controls the wiper operation according to the result of estimating the above-described various conditions of the sensing surface 2a by the matching part 62. It should be noted that the wiper controlling part 7 may control the wiper operation only according to the estimation result by the matching part 62 or may determine how the wiper is operated with reference to signals obtained from other sensors installed in the vehicle.

The wiper controlling part 7 operates the wiper when, for example, the matching part 62 estimates that a raindrop is lying on the sensing surface 2a. Incidentally, the present embodiment does not illustrate an example of discriminating between rainfall conditions (the intensities of rain). However, since the displacement status pattern varies depending on the intensities of rain, it also may be possible to estimate the rainfall conditions from the feature values of the displacement status data and operate the wiper at appropriate wiping intervals for the rainfall conditions. When it is estimated that the condensation has formed, the wiper is not operated. This is because usual condensation rarely obstructs the driver's view, and if the wiper is operated, the driver is likely to recognize it as a malfunction of the wiper. However, in the case where the condensation that obstructs the driver's view has formed, it is necessary to operate the wiper. In other words, when the matching part 62 estimates that the condensation has formed on the sensing surface 2a and the output of the photo-detector 4 changes considerably within a short period of time, it is preferable that the wiper controlling part 7 assumes that the driver's view is obstructed and operates the wiper.

When it is estimated that the running water is passing, the wiper is operated so as to remove the running water. In other words, when the matching part 62 estimates that the water is running on the sensing surface 2a and the output of the photodetector 4 changes considerably within a short period of time, it is preferable that the wiper controlling part 7 assumes that the driver's view is obstructed and operates the wiper. Incidentally, when the matching part 62 still estimates that the water is running on the sensing surface 2a immediately after operating the wiper, it is preferable to assume that the running water continues passing over the sensing surface 2a and operate the wiper continuously. Further, if the running water is such that the driver's view is deteriorated remarkably, the wiping is carried out at rapid intervals. If not, the wiping frequency does not have to be high.

When it is estimated that the finger has contacted, the wiper is not operated from the halted state. This is to prevent the wiper from being operated when, for example, a worker at a gas station is about to clean the windshield before an engine is stopped. Incidentally, it is possible to determine more reliably whether or not the vehicle is at a halt by combining a signal indicating the status of a parking brake or an emergency brake of that vehicle, an open signal of a fuel cap, a parking range input signal, a hazard input signal, etc.

Although an embodiment of the present invention has been described above, the embodiment of the present invention is not limited to the above-described example but can be modified in various ways.

INDUSTRIAL APPLICABILITY

The present invention is industrially applicable as a vehicular wiper controlling apparatus capable of a wiper control in response to the change in the condition of a sensing surface.

The invention claimed is:

1. A vehicular wiper controlling apparatus comprising:
an optical part comprising a photo emission element that irradiates light to a sensing surface, and a photo-detector that is arranged at a position receiving the light emitted from the photo emission element and reflected by the sensing surface, the sensing surface being part of a surface of a windshield glass of a vehicle;
an estimating part that estimates a condition of the sensing surface by analyzing a change in an output signal of the photo-detector; and
a wiper controlling part that controls an operation of a wiper installed in the vehicle according to an estimation result signal outputted from the estimating part;
wherein the estimating part comprises
a displacement status data generating part that calculates displacement status data representing a displacement status of the output signal of the photo-detector respectively based on a plurality of sampling data trains obtained from the output signal of the photo-detector at plural kinds of sampling periods in both of a period in which the wiper is in operation and a period in which the wiper is not in operation,
a pattern data storing part that stores in advance displacement status pattern data representing a displacement status of the output signal of the photo-detector when a lying object or a contact object is present on the sensing surface and displacement status pattern data representing a displacement status of the output signal of the photo-detector when a wiper blade passes over the sensing surface, and
a matching part that compares the displacement status data calculated by the displacement status data generating part with the displacement status pattern data stored in the pattern data storing part and outputs the estimation result signal representing the condition of the sensing surface.

2. The vehicular wiper controlling apparatus according to claim 1, wherein the pattern data storing part stores in advance plural kinds of displacement status pattern data regarding a form of water lying on or contacting the sensing surface as the displacement status pattern data representing the displacement status of the output signal of the photo-detector when the lying object or the contact object is present on the sensing surface.

3. The vehicular wiper controlling apparatus according to claim 1, wherein the displacement status data generating part generates a sampling data train consisting of m sampling data (where $m=2^{a \times b}$, with a and b being an integer) obtained at a predetermined clock period N and a sampling data train consisting of $2^b$, $2^{b-1}$, ..., $(m/2^{a \times c})$ sampling data obtained at clock periods obtained by multiplying the clock period N respectively by $2^a$, $2^{a \times 2}$, ..., $2^{a \times c}$ (where c is an integer not greater than b) as the plurality of sampling data trains.

4. The vehicular wiper controlling apparatus according to claim 1, wherein the displacement status data generating part calculates displacement amounts of sampling data respectively in the plurality of sampling data trains as the displacement status data.

5. The vehicular wiper controlling apparatus according to claim 1, wherein the displacement status data generating part calculates a displacement amount difference representing a difference between displacement amounts of sampling data respectively in the plurality of sampling data trains as the displacement status data.

6. The vehicular wiper controlling apparatus according to claim 1, wherein the displacement status data generating part calculates successive displacement amounts representing an amount that the sampling data are displaced successively in either a positive direction or a negative direction respectively in the plurality of sampling data trains as the displacement status data.

7. The vehicular wiper controlling apparatus according to claim 1, wherein the displacement status data generating part calculates the number of successive displacements representing the number of times that the sampling data are displaced successively in either a positive direction or a negative direction respectively in the plurality of sampling data trains as the displacement status data.

8. The vehicular wiper controlling apparatus according to claim 1, wherein the pattern data storing part stores in advance displacement status pattern data representing a displacement status of the output signal of the photo-detector when a lying object or a contact object is present on a water-repellent sensing surface, displacement status pattern data representing a displacement status of the output signal of the photo-detector when the wiper blade passes over a water-repellent sensing surface, displacement status pattern data representing a displacement status of the output signal of the photo-detector when a lying object or a contact object is present on a hydrophilic sensing surface and displacement status pattern data representing a displacement status of the output signal of the photo-detector when the wiper blade passes over a hydrophilic sensing surface.

9. The vehicular wiper controlling apparatus according to claim 1, wherein the pattern data storing part further stores displacement status pattern data representing a displacement status of the output signal of the photo-detector when a human hand contacts the sensing surface.

10. The vehicular wiper controlling apparatus according to claim 1, wherein the pattern data storing part further stores displacement status pattern data representing a displacement status of the output signal of the photo-detector when an oil film is lying on the sensing surface.

11. A vehicular wiper controlling method of inputting an output signal of a photo-detector from an optical part comprising a photo emission element that irradiates light to a sensing surface, which is part of a surface of a windshield glass of a vehicle, and the photo-detector that is arranged at a position receiving the light emitted from the photo emission element and reflected by the sensing surface, estimating a condition of the sensing surface by analyzing a change in the output signal, and controlling an operation of a wiper installed in the vehicle according to an estimation result, the method comprising:

a displacement status data generating step of calculating displacement status data representing a displacement status of the output signal of the photo-detector respectively based on a plurality of sampling data trains obtained from the output signal of the photo-detector at plural kinds of sampling periods in both of a period in which the wiper is in operation and a period in which the wiper is not in operation; and a matching step of comparing the displacement status data calculated in the displacement status data generating step with displacement status pattern data in a pattern data storing part that stores in advance displacement status pattern data representing a displacement status of the output signal of the photo-detector when a lying object or a contact object is present on the sensing surface and displacement status pattern data representing a displacement status of the output signal of the photo-detector when a wiper blade passes over the sensing surface, and obtaining the estimation result representing the condition of the sensing surface.

* * * * *